Figure 1:
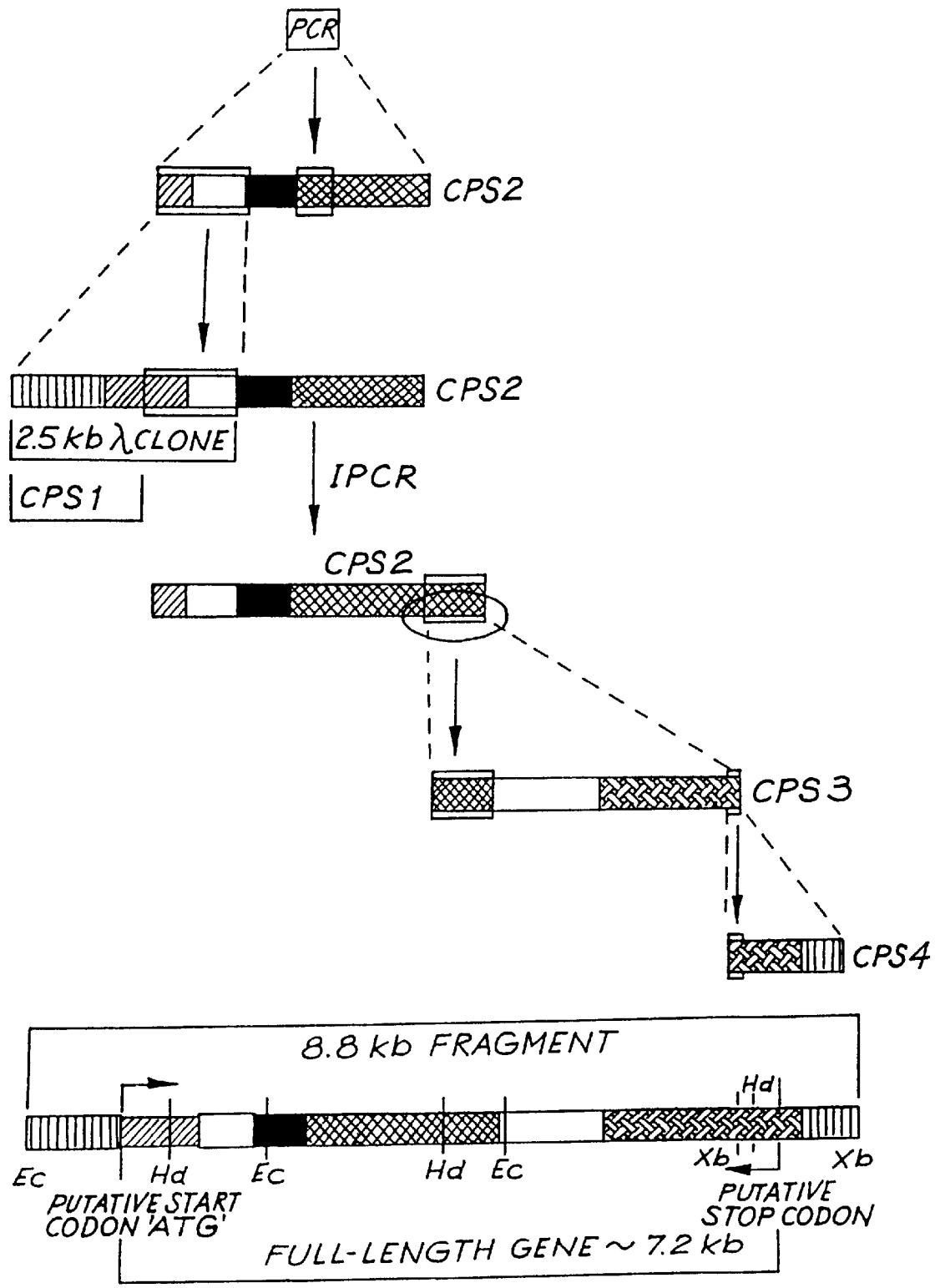

United States Patent [19]

Stewart et al.

[11] Patent Number: 5,849,573
[45] Date of Patent: Dec. 15, 1998

[54] NUCLEOTIDE SEQUENCE ENCODING CARBAMOYL PHOSPHATE SYNTHETASE II

[75] Inventors: Thomas Stanley Stewart; Maria Vega Flores; William James O'Sullivan, all of Sydney, Australia

[73] Assignee: Unisearch Limited, Kensington, Australia

[21] Appl. No.: 446,855

[22] PCT Filed: Dec. 2, 1993

[86] PCT No.: PCT/AU93/00617

§ 371 Date: Jul. 6, 1995

§ 102(e) Date: Jul. 6, 1995

[87] PCT Pub. No.: WO94/12643

PCT Pub. Date: Jun. 9, 1994

[30] Foreign Application Priority Data

Dec. 3, 1992 [AU] Australia ................................. PL6206
Dec. 16, 1992 [AU] Australia ................................. PL6380

[51] Int. Cl.$^6$ .......................... C07H 21/04; C12N 15/30; C12N 15/52; C12N 15/70
[52] U.S. Cl. .................. 435/320.1; 435/69.1; 435/172.3; 435/194; 536/23.1; 536/23.2; 536/23.7
[58] Field of Search ............................ 435/6, 69.1, 69.2, 435/71.1, 71.2, 91.1, 91.31, 172.3, 252.33, 254.2, 258.2, 320.1, 194; 530/350; 536/23.2, 23.7, 24.5; 935/9

[56] References Cited

U.S. PATENT DOCUMENTS 5,585,479  12/1996  Hoke et al. ............................. 536/24.5

OTHER PUBLICATIONS

J.P. Schofield,. "Molecular Studies on an ancient gene encoding for carbomoyl–phosphate synthetase" Clinical Science (1993), vol. 84, pp. 119–128.

H. Nyunoya et al. "Characterization and derivation of the gene encoding for mitochondrial carbamyl phosphate synthetase I of Rat" Journal of Biological Chemistry (1985), vol. 260 No. 15, pp. 9346–9356.

G. Elgar et al. "Carbamoyl phosphate synthetase (CPSase) in the PYRI1–3 multigene . . . " DNA sequence, vol. 2, (1992) Harwood Academic Publisher (UK), pp. 219–226.

C.J. Lustry et al. "Yeast carbamyl phosphate synthetase" Journal of Biological Chemistry, vol. 258, No. 23, (10 Dec. 1983), pp. 14466–14472.

Chansiri et al. "The structural gene for carbamoyl phosphate synthetase from the protozoan parasite *Babesia bovis*" Mol. Biochem. Parasitol. 74: 239–243, Dec. 1995.

Gewirtz et al. "Facilitating oligonucleotide delivery: Helping antisense deliver on its promise" Proc. Natl. Acad. Sci. USA 93: 3161–3164, Apr. 1996.

Sambrook et al. "Molecular cloning: A Laboratory manual, second ed." Cold Spring Harbnor Laboratory Press. pp. 8.51–8.52. 1989.

Lewin. "Genes IV" Oxford University Press, New York. pp. 506–507, 1990.

Stull et al. Antigene, ribozyme and aptamer nucleic acid drugs: Prospects and Progress. Pharm. Res. 12(4): 465–483, Apr. 1995.

*Primary Examiner*—John L. LeGuyader
*Assistant Examiner*—Thomas G. Larson
*Attorney, Agent, or Firm*—Nixon & Vanderhye

[57] ABSTRACT

The present invention provides a nucleotide sequence encoding carbamoyl phosphate synthetase II of *Plasmodium falciparum*. Carbamoyl phosphate synthetase II catalyses the first committed and rate-limiting step in the de novo pyrimidine biosynthetic pathway. *P. falciparum* relies exclusively on pyrimidine synthesis de novo because of its inability to salvage pyrimidines. Mature human red blood cells, however, have no recognised requirement for a pyrimidine nucleotide. Accordingly, this enzyme represents a prime chemotherapeutic locus. The present invention relates to the use of the sequence encoding carbamoyl phosphate synthetase II in the recombinant production of carbamoyl phosphate synthetase II and to antisense molecules, ribozymes and other gene inactivation agents designed from this sequence.

4 Claims, 1 Drawing Sheet

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 8920 base pairs
        ( B ) TYPE: nucleic acid
        ( C ) STRANDEDNESS: single
        ( D ) TOPOLOGY: linear ( i i ) MOLECULE TYPE: genomic ( x i ) SEQUENCE DESCRIPTION: SEQ ID NO:1:

```
GAATTCCTTC  AGCCAAAAAA  AATGACAACG  CAAATTTTAA  GAAAAGAAAA  ACAATCGACT        60
CGTCTTTGAA  TGAGGTTAGA  AATTCGATAC  GTGAAAGGGA  CTTAAGAAGG  CTTAACAGAG       120
AAAGAGTAA   AATCTTATAA  GCATTTGAAG  GAAAAAATAA  TAAAATAAAA  AATAAAAAG        180
ATAAAAAATA  TTTATATTTG  ATATGTAGTA  TATATAATGA  TTATTCATAT  TAATAACATA       240
GATAAAAAAC  TTTTTTTTTT  TTTTTTTTC   TTTATATTTA  TTAACAATAC  ATTTAAGTTA       300
TTTTATATAT  ATATATATAT  ATATATATAT  ATATATATAT  ATATATGTTT  GTGTGTTCAT       360
TTGTTTATAA  AATTACTTGA  AATATAAAAC  TTATTAATAT  ATTTCCAATT  AATATGAATA       420
CAATTATTAA  TATTTTGATG  TGTACACATT  AATATAGTTT  TACACTTCTT  ATAATAAAAC       480
CATCCTATAT  ATTATACACA  ATATATAATA  CTCCCCAATA  TTGTGGTTCC  TATAATTTTA       540
TTTATATATT  TATTTATTAA  TTTATTCATT  TATTTATTTT  TTTTCTTAGT  TTATAAAATA       600
GTAATTCTAC  TAATTTAAAA  AAAAAAAAAA  AAAAAAAAA   AAAAAGAAAA  AAAAAAAATT       660
TACATATGAA  AAATGAACTT  GTATATGTAA  ATTTATAAAT  ATTTAAACA   TAAATATAAA       720
TGTATAAAAA  AAAAAAAGAA  AAATGGGAAA  AAATAATATA  GATATATATA  TAAATATATA       780
TATATATATA  ATTATTGGGG  ATATTCTCTG  AATCATAGGT  CTTAAACAGT  TTTATTCTTT       840
TAACATCACA  AAGTTGTTAT  TAAAAGTATA  TATATCTTAT  TGGTTCCTAT  ATAAAACTAT       900
AGTATTCTAT  AATATATTCT  GTATATTTCA  TTTTATCATT  TGTAAGCAAT  CCCTATTTAT       960
TATAATTATT  ATTTTTTTTT  TTATAAAAGA  GGTATAAAAC  AGTTTATTCA  ATTTTTTTCC      1020
TAAAGGAGCA  ACCTTCAGTC  AATTTACATT  TTCCACCGGT  TGGTTGGCAC  AACATAATGT      1080
TACAGCTAAA  AAAAGAAAGA  AAAAAAAAAA  AAAAAAAAAA  AAAAAAAAAA  ATATATATAT      1140
ATATATATAT  ATACATAA    TATGTACAAT  GCTACCATAC  AAGTATATAA  ATTTTTCAAC      1200
ATTGTTGTGA  TGTTGCATTT  TTCTTATGTA  TATTTCTTTT  AAATATAATT  TATATATATA      1260
TATATATATA  TATATATATA  TATTTGTTCT  TATAGATTTT  AAAACAGTTG  GGAGGTTAAT      1320
TCTTGAAGAT  GGTAACGAAT  TTGTAGGGTA  CAGTGTAGGT  TACGAAGGGT  GTAAAGGAAA      1380
TAATAGTATA  TCATGTCATA  AGGAGTATAG  AAATATTATT  AATAATGATA  ATAGCAAGAA      1440
TAGTAATAAT  TCATTTTGTA  ATAATGAAGA  AAACAATTTG  AAAGATGATT  TATTATATAA      1500
AAATAGTCGA  TTAGAAAATG  AAGATTTTAT  TGTTACAGGT  GAAGTTATAT  TTAATACAGC      1560
TATGGTTGGA  TATCCTGAAG  CTTTAACGGA  CCCAAGTTAT  TTTGGTCAAA  TATTAGTTTT      1620
AACATTTCCT  TCTATTGGTA  ATTATGGTAT  TGAAAAAGTA  AAACATGATG  AAACGTTTGG      1680
ATTAGTACAA  AATTTTGAAA  GTAATAAAAT  TCAAGTACAA  GGTTTAGTTA  TTTGTGAATA      1740
TTCGAAGCAA  TCATATCATT  ACAATTCTTA  TATTACCTTA  AGTGAATGGT  TAAAGATTTA      1800
```

```
TAAAATTCCA TGTATAGGTG GTATAGATAC AAGAGCCTTA ACAAAACTTT TAAGAGAAAA   1860
AGGTAGTATG TTAGGTAAAA TAGTTATATA TAAAAACAGA CAACATATTA ATAAATTATA   1920
TAAAGAAATT AATCTTTTTG ATCCTGGTAA TATAGATACT CTAAATATG TATGTAATCA    1980
TTTTATACGT GTTATTAAGT TGAATAATAT TACATATAAT TATAAAAATA AGGAAGAATT   2040
TAATTATACC AATGAAATGA TTACTAATGA TTCTTCAATG GAAGATCATG ATAATGAAAT   2100
TAATGGTAGT ATTTCTAATT TTAATAATTG TCCAAGTATC TCTAGTTTTG ATAAAAGTGA   2160
ATCGAAAAAT GTTATTAATC ATACATTGTT AAGAGATAAA ATGAACCTAA TAACTTCATC   2220
TGAAGAATAT CTGAAAGATC TTCATAATTG TAATTTTAGT AATAGTAGTG ATAAAAATGA   2280
TTCTTTTTTT AAGTTATATG GTATATGTGA ATATGATAAA TATTTAATTG ACCTTGAAGA   2340
AAATGCTAGC TTTCATTATA ATAATGTAGA TGAATATGGA TATTATGATG TTAATAAAAA   2400
TACAAATATT CTATCTAATA ATAAAATAGA ACAAACAAC AATAACGAAA ATAACAAAAA    2460
TAACAAAAAT AACAACAATA ACGAGGTTGA TTATATAAAG AAAGATGAGG ATAATAATGT   2520
CAATAGTAAG GTCTTTTATA GCCAATATAA TAATAATGCA CAAAATAATG AACATACCGA   2580
ATTTAATTTA AATAATGATT ATTCTACTTA TATTAGAAAG AAAATGAAAA ATGAAGAATT   2640
CCTTAATTTG GTAAACAAAA GAAAGTAGA CCATAAAGAA AAAATTATTG TTATTGTTGA    2700
TTGTGGTATT AAAAATAGTA TAATCAAAAA TTAATAAGA CACGGTATGG ATCTTCCATT    2760
AACATATATT ATTGTACCTT ATTATTACAA TTTTAATCAT ATAGATTATG ATGCAGTTCT   2820
TTTATCTAAT GGTCCTGGAG ATCCTAAAAA GTGTGATTTC CTTATAAAAA ATTTGAAAGA   2880
TAGTTTAACA AAAAATAAAA TTATATTTGG TATTTGTTTA GGTAATCAAC TATTAGGTAT   2940
ATCATTAGGT TGTGACACAT ATAAAATGAA ATATGGTAAT AGAGGTGTTA ATCAACCCGT   3000
AATACAATTA GTAGATAATA TATGTTACAT TACCTCACAA AATCATGGAT ACTGTTTAAA   3060
GAAAAAATCA ATTTTAAAAA GAAAAGAGCT TGCGATTAGT TATATAAATG CTAATGATAA   3120
ATCTATAGAA GGTATTTCAC ATAAAAATGG AAGATTTTAT AGTGTCCAGT TTCATCCTGA   3180
GGGTAATAAT GGTCCTGAAG ATACATCATT TTTATTTAAG AATTTTCTTT TAGATATCTT   3240
TAATAAGAAA AAACAATATA GAGAATATTT AGGATATAAT ATTATTTATA TAAAAAAGAA   3300
AGTGCTTCTT TTAGGTAGTG GTGGTTTATG TATAGGACAA GCAGGAGAAT TCGATTATTC   3360
AGGAACACAA GCAATTAAAA GTTTAAAAGA ATGTGGTATA TATGTTATAT TAGTTAATCC   3420
TAACATAGCA ACTGTTCAAA CATCAAAAGG TTTGGCAGAT AAGGTATACT TTTTACCAGT   3480
TAATTGTGAA TTTGTAGAAA AAATTATTAA AAAGGAAAAA CCTGATTTTA TTTTATGTAC   3540
ATTTGGTGGT CAGACAGCTT TAAATTGTGC TTTAATGTTA GATCAAAAAA AAGTATTGAA   3600
AAAGAATAAT TGTCAATGTT TAGGTACATC TTTAGAATCT ATAAGAATAA CAGAAAATAG   3660
AACATTATTT GCTGAAAAAT TAAAGAAAT TAATGAAAGA ATAGCTCCAT ATGGTAGTGC    3720
AAAAAATGTT AATCAAGCTA TTGATATAGC TAATAAAATA GGATATCCAA TATTAGTACG   3780
TACAACATTT TCGTTAGGAG GATTAAATAG TAGTTTCATA AATAATGAAG AAGAACTTAT   3840
CGAAAAATGT AATAAAATAT TTTTACAAAC TGATAATGAA ATATTTATAG ATAAATCATT   3900
ACAAGGATGG AAAGAAATAG AATATGAATT ATTAAGAGAT AATAAAAATA ATTGTATAGC   3960
TATATGTAAT ATGGAAAATA TAGATCCATT AGGTATACAT ACAGGAGATA GTATAGTTGT   4020
TGCACCTTCA CAAACATTAA GTAATTATGA ATATTATAAA TTTAGAGAAA TAGCATTAAA   4080
GGTAATTACA CATTTAAATA TTATAGGAGA ATGTAATATA CAATTTGGTA TAAATCCACA   4140
AACAGGAGAA TATTGTATTA TTGAAGTTAA TGCTAGGCTT AGTAGAAGTT CAGCATTAGC   4200
```

-continued

| | | | | | | |
|---|---|---|---|---|---|---|
| TTCTAAAGCT | ACTGGTTATC | CACTTGCTTA | TATATCAGCA | AAAATAGCCT | TGGGATATGA | 4260 |
| TTTGATAAGT | TTAAAAAATA | GCATAACTAA | AAAAACAACT | GCCTGTTTTG | AACCCTCTCT | 4320 |
| AGATTACATT | ACAACAAAAA | TACCACGATG | GGATTTAAAT | AAATTTGAGT | TTGCTTCTAA | 4380 |
| TACAATGAAT | AGTAGTATGA | AAAGTGTAGG | AGAAGTTATG | TCTATAGGTA | GAACCTTTGA | 4440 |
| AGAATCTATA | CAAAAATCTT | TAAGATGTAT | TGATGATAAT | TATTTAGGAT | TTAGTAATAC | 4500 |
| GTATTGTATA | GATTGGGATG | AAAAGAAAAT | TATTGAAGAA | TTAAAAAATC | CATCACCAAA | 4560 |
| AAGAATTGAT | GCTATACATC | AAGCTTTCCA | TTTAAATATG | CCTATGGATA | AAATACATGA | 4620 |
| GCTGACACAT | ATTGATTATT | GGTTCTTACA | TAAATTTTAT | AATATATATA | ATTTACAAAA | 4680 |
| TAAGTTGAAA | ACGTTAAAAT | TAGAGCAATT | ATCTTTTAAT | GATTGAAGT | ATTTTAAGAA | 4740 |
| GCATGGTTTT | AGTGATAAGC | AAATAGCTCA | CTACTTATCC | TTCAACACAA | GCGATAATAA | 4800 |
| TAATAATAAT | AATAATATTA | GCTCATGTAG | GGTTACAGAA | AATGATGTTA | TGAAATATAG | 4860 |
| AGAAAAGCTA | GGATTATTTC | CACATATTAA | AGTTATTGAT | ACCTTATCAG | CCGAATTTCC | 4920 |
| GGCTTTAACT | AATTATTTAT | ATTTAACTTA | TCAAGGTCAA | GAACATGATG | TTCTCCCATT | 4980 |
| AAATATGAAA | AGGAAAAAGA | TATGCACGCT | TAATAATAAA | CGAAATGCAA | ATAAGAAAAA | 5040 |
| AGTCCATGTC | AAGAACCACT | TATATAATGA | AGTAGTTGAT | GATAAGGATA | CACAATTACA | 5100 |
| CAAAGAAAAT | AATAATAATA | ATAAATGAA | TTCTGGAAAT | GTAGAAAATA | AATGTAAATT | 5160 |
| GAATAAAGAA | TCCTATGGCT | ATAATAATTC | TTCTAATTGT | ATCAATACAA | ATAATATTAA | 5220 |
| TATAGAAAAT | AATATTTGTC | ATGATATATC | TATAAACAAA | AATATAAAG | TTACAATAAA | 5280 |
| CAATTCCAAT | AATTCTATAT | CGAATAATGA | AAATGTTGAA | ACAAACTTAA | ATTGTGTATC | 5340 |
| TGAAAGGGCC | GGTAGCCATC | ATATATATGG | TAAAGAAGAA | AAGAGTATAG | GATCTGATGA | 5400 |
| TACAAATATT | TTAAGTGCAC | AAAATTCAAA | TAATAACTTT | TCATGTAATA | ATGAGAATAT | 5460 |
| GAATAAAGCA | AACGTTGATG | TTAATGTACT | AGAAAATGAT | ACGAAAAAC | GAGAAGATAT | 5520 |
| AAATACTACA | ACAGTATTTA | TGGAAGGTCA | AAATAGTGTT | ATTAATAATA | AGAATAAAGA | 5580 |
| GAATAGTTCT | TTATTGAAAG | GTGATGAAGA | AGATATTGTG | ATGGTAAATT | TAAAAAAGGA | 5640 |
| AAATAATTAT | AATAGTGTAA | TTAATAATGT | AGATTGTAGG | AAAAAGGATA | TGGATGGAAA | 5700 |
| AAATATAAAT | GATGAATGTA | AAACATATAA | GAAAAATAAA | TATAAGATA | TGGGATTAAA | 5760 |
| TAATAATATA | GTAGATGAGT | TATCCAATGG | AACATCACAT | TCAACTAATG | ATCATTTATA | 5820 |
| TTTAGATAAT | TTTAATACAT | CAGATGAAGA | AATAGGGAAT | AATAAAAATA | TGGATATGTA | 5880 |
| TTTATCTAAG | GAAAAAAGTA | TATCTAATAA | AAACCCTGGT | AATTCTTATT | ATGTTGTAGA | 5940 |
| TTCCGTATAT | AATAATGAAT | ACAAAATTAA | TAAGATGAAA | GAGTTAATAG | ATAACGAAAA | 6000 |
| TTTAAATGAT | GAATATAATA | ATAATGTTAA | TATGAATTGT | TCTAATTATA | ATAATGCTAG | 6060 |
| TGCATTTGTA | AATGGAAAGG | ATAGAAATGA | TAATTTAGAA | AATGATTGTA | TTGAAAAAAA | 6120 |
| TATGGATCAT | ACATACAAAC | ATTATAATCG | TTTAAACAAT | CGTAGAAGTA | CAAATGAGAG | 6180 |
| GATGATGCTT | ATGGTAAACA | ATGAAAAAGA | GAGCAATCAT | GAGAAGGGCC | ATAGAAGAAA | 6240 |
| TGGTTTAAAT | AAAAAAAATA | AAGAAAAAAA | TATGGAAAAA | AATAAGGGAA | AAAATAAAGA | 6300 |
| CAAAAGAAT | TATCATTATG | TTAATCATAA | AAGGAATAAT | GAATATAATA | GTAACAATAT | 6360 |
| TGAATCGAAG | TTTAATAATT | ATGTTGATGA | TATAAATAAA | AAGAATATT | ATGAAGATGA | 6420 |
| AAATGATATA | TATTATTTTA | CACATTCGTC | ACAAGGTAAC | AATGACGATT | TAAGTAATGA | 6480 |
| TAATTATTTA | AGTAGTGAAG | AATTGAATAC | TGATGAGTAT | GATGATGATT | ATTATTATGA | 6540 |
| TGAAGATGAA | GAAGATGACT | ATGACGATGA | TAATGATGAT | GATGATGATG | ATGATGATGA | 6600 |

| | | | | | | |
|---|---|---|---|---|---|---|
| TGGGGAGGAT | GAGGAGGATA | ATGATTATTA | TAATGATGAT | GGTTATGATA | GCTATAATTC | 6660 |
| TTTATCATCT | TCAAGAATAT | CAGATGTATC | ATCTGTTATA | TATTCAGGGA | ACGAAAATAT | 6720 |
| ATTTAATGAA | AAATATAATG | ATATAGGTTT | TAAAATAATC | GATAATAGGA | ATGAAAAAGA | 6780 |
| GAAAGAGAAA | AAGAAATGTT | TTATTGTATT | AGGTTGTGGT | TGTTATCGTA | TTGGTAGTTC | 6840 |
| TGTAGAATTT | GATTGGAGTG | CTATACATTG | TGTAAAGACC | ATAAGAAAAT | TAAACCATAA | 6900 |
| AGCTATATTA | ATAAATTGTA | ACCCAGAAAC | TGTAAGTACA | GATTATGATG | AAAGTGATCG | 6960 |
| TCTATATTTT | GATGAAATAA | CAACAGAAGT | TATAAAATTT | ATATATAACT | TTGAAAATAG | 7020 |
| TAATGGTGTG | ATTATAGCTT | TTGGTGGACA | AACATCAAAT | AATTTAGTAT | TTAGTTTATA | 7080 |
| TAAAAATAAT | GTAAATATAT | TAGGATCAGT | GCACAAAGTG | TTGATTGTTG | TGAAAATAGG | 7140 |
| AATAAATTTT | CGCACTTATG | TGATTCTTAA | AATTGATCAA | CCGAAATGGA | ATAAATTTAC | 7200 |
| AAAATTATCC | AAGGCTATAC | AATTTGCTAA | TGAGGTAAAA | TTTCCTGTAT | TAGTAAGACC | 7260 |
| ATCGTATGTA | TTATCTGGTG | CAGCTATGAG | AGTTGTAAAT | TGTTTTGAAG | AATTAAAAAA | 7320 |
| CTTTTTAATG | AAGGCAGCTA | TTGTTAGTAA | AGATAATCCT | GTTGTAATAT | CAAAATTTAT | 7380 |
| TGAGAATGCT | AAAGAAATAG | AAATAGATTG | TGTTAGTAAA | AATGGTAAAA | TAATTAATTA | 7440 |
| TGCTATATCT | GAACATGTTG | AAAATGCTGG | TGTACATTCA | GGTGATGCAA | CATTAATATT | 7500 |
| ACCTGCACAA | AATATATATG | TTGAAACACA | TAGGAAAATA | AAGAAAATAT | CCGAAAAGAT | 7560 |
| TTCAAAATCA | TTAAATATAT | CTGGTCCATT | TAATATACAA | TTTATATGTC | ATCAAAATGA | 7620 |
| AATAAAAATT | ATTGAATGTA | ATTTAAGAGC | ATCTAGAACT | TTTCCATTTA | TATCAAAAGC | 7680 |
| TCTAAATCTA | AACTTTATAG | ATTTAGCTAC | AAGGATATTA | ATGGGTTATG | ACGTCAAACC | 7740 |
| AATTAATATA | TCATTAATTG | ATTTAGAATA | TACAGCTGTA | AAAGCACCGA | TTTTCTCATT | 7800 |
| TAATAGATTA | CATGGATCAG | ATTGTATACT | AGGTGTAGAA | ATGAAATCTA | CAGGTGAAGT | 7860 |
| AGCATGTTTT | GGTTAAAATA | AATATGAAGC | TTTATTAAAA | TCATTAATAG | CTACAGGTAT | 7920 |
| GAAGTTACCC | AAAAAATCAA | TACTTATAAG | TATTAAAAAT | TAAATAATA | AATTAGCTTT | 7980 |
| TGAAGAACCG | TTCCAATTAT | TATTTTTAAT | GGGATTTACA | ATATATGCGA | CTGAAGGTAC | 8040 |
| GTATGATTTC | TACTCTAAAT | TTTTAGAATC | TTTTAATGTT | AATAAAGGTT | CTAAATTTCA | 8100 |
| TCAAAGACTT | ATTAAAGTTC | ATAATAAAAA | TGCAGAAAAT | ATATCACCAA | ATACAACAGA | 8160 |
| TTTAATTATG | AATCATAAAG | TTGAAATGGT | TATTAATATA | ACTGATACAT | TAAAAACAAA | 8220 |
| GGTTAGTTCA | AATGGTTATA | AAATTAGAAG | ATTAGCATCA | GATTTCCAGG | TTCCTTTAAT | 8280 |
| AACTAATATG | AAACTTTGTT | CTCTTTTTAT | TGACTCATTA | TATAGAAAAT | TCTCAAGACA | 8340 |
| AAAGGAAAGA | AAATCATTCT | ATACCATAAA | GAGTTATGAC | GAATATATAA | GTTTGGTATA | 8400 |
| AGCAAGAAAT | TATTCAATAA | ATTCGATTTA | ACATTACTTA | TTTATGTATT | TATTAACTTT | 8460 |
| CATTCCATAA | CAACATGAAA | AGTATAAATA | TATAAATAGT | AATATATAAT | ATATAATATA | 8520 |
| TATATATATA | TATATATATA | TATTTATTTA | TTTAATTATA | TTTACGTTTA | AATATTAATA | 8580 |
| AATGTTTTTA | TTAAATATGA | TCATTAATTT | ATATTGATTT | ATTTTTTTAT | AAATTTTTGT | 8640 |
| TATATATACA | AATTTTATTT | ATTCACTCAT | ATGTATAAAC | CAAAATGGTT | TTTTCAATTT | 8700 |
| ACAAATAATT | TTATAATTTT | AATAAATTTA | TTAATTATAA | AAAAATAAA | AATATATAAA | 8760 |
| CATTAAAATG | TATAAATTCT | TTTAATTATA | TAATAATTTA | TAAATGTTAT | GATTTTTTTA | 8820 |
| AAAAATTCAA | CGAAAAAAAA | GAGGAACTGT | ATATACAAAA | GGGACTATAT | ATATGTATAT | 8880 |
| ATATATATAT | ATATATATGT | TTTTTTTTCC | TTATTCTAGA | | | 8920 |

( 2 ) INFORMATION FOR SEQ ID NO:2:

(i) SEQUENCE CHARACTERISTICS:
  (A) LENGTH: 2391 amino acids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO:2:

```
Met Tyr Ile Ser Phe Lys Tyr Asn Leu Tyr Ile Tyr Ile Tyr Ile Tyr
 1               5                  10                  15
Ile Tyr Ile Phe Val Leu Ile Asp Phe Lys Thr Val Gly Arg Leu Ile
             20                  25                  30
Leu Glu Asp Gly Asn Glu Phe Val Gly Tyr Ser Val Gly Tyr Glu Gly
         35                  40                  45
Cys Lys Gly Asn Asn Ser Ile Ser Cys His Lys Glu Tyr Arg Asn Ile
     50                  55                  60
Ile Asn Asn Asp Asn Ser Lys Asn Ser Asn Ser Phe Cys Asn Asn Asn
 65                  70                  75                  80
Glu Glu Asn Asn Leu Lys Asp Asp Leu Leu Tyr Lys Asn Ser Arg Leu
                 85                  90                  95
Glu Asn Glu Asp Phe Ile Val Thr Gly Glu Val Ile Phe Asn Thr Ala
            100                 105                 110
Met Val Gly Tyr Pro Glu Ala Leu Thr Asp Pro Ser Tyr Phe Gly Gln
            115                 120                 125
Ile Leu Val Leu Thr Phe Pro Ser Ile Gly Asn Tyr Gly Ile Glu Lys
            130                 135                 140
Val Lys His Asp Glu Thr Phe Gly Leu Val Gln Asn Phe Glu Ser Asn
145                 150                 155                 160
Lys Ile Gln Val Gln Gly Leu Val Ile Cys Glu Tyr Ser Lys Gln Ser
                165                 170                 175
Tyr His Tyr Asn Ser Tyr Ile Thr Leu Ser Glu Trp Leu Lys Ile Tyr
            180                 185                 190
Lys Ile Pro Cys Ile Gly Gly Ile Asp Thr Arg Ala Leu Thr Lys Leu
        195                 200                 205
Leu Arg Glu Lys Gly Ser Met Leu Gly Lys Ile Val Ile Tyr Lys Asn
    210                 215                 220
Arg Gln His Ile Asn Lys Leu Tyr Lys Glu Ile Asn Leu Phe Asp Pro
225                 230                 235                 240
Gly Asn Ile Asp Thr Leu Lys Tyr Val Cys Asn His Phe Ile Arg Val
                245                 250                 255
Ile Lys Leu Asn Asn Ile Thr Tyr Asn Tyr Lys Asn Lys Glu Glu Phe
            260                 265                 270
Asn Tyr Thr Asn Glu Met Ile Thr Asn Asp Ser Ser Met Glu Asp His
        275                 280                 285
Asp Asn Glu Ile Asn Gly Ser Ile Ser Asn Phe Asn Asn Cys Pro Ser
    290                 295                 300
Ile Ser Ser Phe Asp Lys Ser Glu Ser Lys Asn Val Ile Asn His Thr
305                 310                 315                 320
Leu Leu Arg Asp Lys Met Asn Leu Ile Thr Ser Ser Glu Glu Tyr Leu
                325                 330                 335
Lys Asp Leu His Asn Cys Asn Phe Ser Asn Ser Ser Asp Lys Asn Asp
            340                 345                 350
Ser Phe Phe Lys Leu Tyr Gly Ile Cys Glu Tyr Asp Lys Tyr Leu Ile
        355                 360                 365
```

```
Asp  Leu  Glu  Glu  Asn  Ala  Ser  Phe  His  Tyr  Asn  Asn  Val  Asp  Glu  Tyr
     370            375                      380

Gly  Tyr  Tyr  Asp  Val  Asn  Lys  Asn  Thr  Asn  Ile  Leu  Ser  Asn  Asn  Lys
385                      390                 395                           400

Ile  Glu  Gln  Asn  Asn  Asn  Glu  Asn  Lys  Asn  Asn  Lys  Asn
                    405                 410                 415

Asn  Asn  Asn  Glu  Val  Asp  Tyr  Ile  Lys  Lys  Asp  Glu  Asp  Asn  Asn  Val
               420                      425                 430

Asn  Ser  Lys  Val  Phe  Tyr  Ser  Gln  Tyr  Asn  Asn  Asn  Ala  Gln  Asn  Asn
          435                 440                      445

Glu  His  Thr  Glu  Phe  Asn  Leu  Asn  Asn  Asp  Tyr  Ser  Thr  Tyr  Ile  Arg
     450                 455                      460

Lys  Lys  Met  Lys  Asn  Glu  Glu  Phe  Leu  Asn  Leu  Val  Asn  Lys  Arg  Lys
465                      470                 475                           480

Val  Asp  His  Lys  Glu  Lys  Ile  Ile  Val  Ile  Val  Asp  Cys  Gly  Ile  Lys
               485                      490                           495

Asn  Ser  Ile  Ile  Lys  Asn  Leu  Ile  Arg  His  Gly  Met  Asp  Leu  Pro  Leu
          500                      505                      510

Thr  Tyr  Ile  Ile  Val  Pro  Tyr  Tyr  Asn  Phe  Asn  His  Ile  Asp  Tyr
          515                 520                      525

Asp  Ala  Val  Leu  Leu  Ser  Asn  Gly  Pro  Gly  Asp  Pro  Lys  Lys  Cys  Asp
     530                 535                      540

Phe  Leu  Ile  Lys  Asn  Leu  Lys  Asp  Ser  Leu  Thr  Lys  Asn  Lys  Ile  Ile
545                      550                 555                           560

Phe  Gly  Ile  Cys  Leu  Gly  Asn  Gln  Leu  Leu  Gly  Ile  Ser  Leu  Gly  Cys
               565                      570                           575

Asp  Thr  Tyr  Lys  Met  Lys  Tyr  Gly  Asn  Arg  Gly  Val  Asn  Gln  Pro  Val
               580                      585                 590

Ile  Gln  Leu  Val  Asp  Asn  Ile  Cys  Tyr  Ile  Thr  Ser  Gln  Asn  His  Gly
          595                 600                      605

Tyr  Cys  Leu  Lys  Lys  Lys  Ser  Ile  Leu  Lys  Arg  Lys  Glu  Leu  Ala  Ile
     610                 615                      620

Ser  Tyr  Ile  Asn  Ala  Asn  Asp  Lys  Ser  Ile  Glu  Gly  Ile  Ser  His  Lys
625                      630                 635                           640

Asn  Gly  Arg  Phe  Tyr  Ser  Val  Gln  Phe  His  Pro  Glu  Gly  Asn  Asn  Gly
                    645                      650                           655

Pro  Glu  Asp  Thr  Ser  Phe  Leu  Phe  Lys  Asn  Phe  Leu  Leu  Asp  Ile  Phe
               660                      665                      670

Asn  Lys  Lys  Lys  Gln  Tyr  Arg  Glu  Tyr  Leu  Gly  Tyr  Asn  Ile  Ile  Tyr
          675                      680                      685

Ile  Lys  Lys  Lys  Val  Leu  Leu  Leu  Gly  Ser  Gly  Gly  Leu  Cys  Ile  Gly
     690                      695                      700

Gln  Ala  Gly  Glu  Phe  Asp  Tyr  Ser  Gly  Thr  Gln  Ala  Ile  Lys  Ser  Leu
705                      710                      715                      720

Lys  Glu  Cys  Gly  Ile  Tyr  Val  Ile  Leu  Val  Asn  Pro  Asn  Ile  Ala  Thr
               725                      730                      735

Val  Gln  Thr  Ser  Lys  Gly  Leu  Ala  Asp  Lys  Val  Tyr  Phe  Leu  Pro  Val
               740                      745                      750

Asn  Cys  Glu  Phe  Val  Glu  Lys  Ile  Ile  Lys  Lys  Glu  Lys  Pro  Asp  Phe
          755                      760                      765

Ile  Leu  Cys  Thr  Phe  Gly  Gly  Gln  Thr  Ala  Leu  Asn  Cys  Ala  Leu  Met
          770                      775                      780

Leu  Asp  Gln  Lys  Lys  Val  Leu  Lys  Lys  Asn  Asn  Cys  Gln  Cys  Leu  Gly
785                      790                      795                      800
```

```
Thr  Ser  Leu  Glu  Ser  Ile  Arg  Ile  Thr  Glu  Asn  Arg  Thr  Leu  Phe  Ala
               805                 810                 815
Glu  Lys  Leu  Lys  Glu  Ile  Asn  Glu  Arg  Ile  Ala  Pro  Tyr  Gly  Ser  Ala
          820                 825                 830
Lys  Asn  Val  Asn  Gln  Ala  Ile  Asp  Ile  Ala  Asn  Lys  Ile  Gly  Tyr  Pro
     835                 840                 845
Ile  Leu  Val  Arg  Thr  Thr  Phe  Ser  Leu  Gly  Gly  Leu  Asn  Ser  Ser  Phe
850                      855                 860
Ile  Asn  Asn  Glu  Glu  Glu  Leu  Ile  Glu  Lys  Cys  Asn  Lys  Ile  Phe  Leu
865                 870                 875                           880
Gln  Thr  Asp  Asn  Glu  Ile  Phe  Ile  Asp  Lys  Ser  Leu  Gln  Gly  Trp  Lys
               885                 890                           895
Glu  Ile  Glu  Tyr  Glu  Leu  Leu  Arg  Asp  Asn  Lys  Asn  Asn  Cys  Ile  Ala
               900                 905                 910
Ile  Cys  Asn  Met  Glu  Asn  Ile  Asp  Pro  Leu  Gly  Ile  His  Thr  Gly  Asp
          915                 920                 925
Ser  Ile  Val  Val  Ala  Pro  Ser  Gln  Thr  Leu  Ser  Asn  Tyr  Glu  Tyr  Tyr
     930                 935                 940
Lys  Phe  Arg  Glu  Ile  Ala  Leu  Lys  Val  Ile  Thr  His  Leu  Asn  Ile  Ile
945                 950                 955                           960
Gly  Glu  Cys  Asn  Ile  Gln  Phe  Gly  Ile  Asn  Pro  Gln  Thr  Gly  Glu  Tyr
                    965                 970                           975
Cys  Ile  Ile  Glu  Val  Asn  Ala  Arg  Leu  Ser  Arg  Ser  Ser  Ala  Leu  Ala
               980                 985                 990
Ser  Lys  Ala  Thr  Gly  Tyr  Pro  Leu  Ala  Tyr  Ile  Ser  Ala  Lys  Ile  Ala
          995                 1000                1005
Leu  Gly  Tyr  Asp  Leu  Ile  Ser  Leu  Lys  Asn  Ser  Ile  Thr  Lys  Lys  Thr
     1010                1015                1020
Thr  Ala  Cys  Phe  Glu  Pro  Ser  Leu  Asp  Tyr  Ile  Thr  Thr  Lys  Ile  Pro
1025                1030                1035                          1040
Arg  Trp  Asp  Leu  Asn  Lys  Phe  Glu  Phe  Ala  Ser  Asn  Thr  Met  Asn  Ser
               1045                1050                1055
Ser  Met  Lys  Ser  Val  Gly  Glu  Val  Met  Ser  Ile  Gly  Arg  Thr  Phe  Glu
               1060                1065                1070
Glu  Ser  Ile  Gln  Lys  Ser  Leu  Arg  Cys  Ile  Asp  Asp  Asn  Tyr  Leu  Gly
          1075                1080                1085
Phe  Ser  Asn  Thr  Tyr  Cys  Ile  Asp  Trp  Asp  Glu  Lys  Lys  Ile  Ile  Glu
     1090                1095                1100
Glu  Leu  Lys  Asn  Pro  Ser  Pro  Lys  Arg  Ile  Asp  Ala  Ile  His  Gln  Ala
1105                1110                1115                          1120
Phe  His  Leu  Asn  Met  Pro  Met  Asp  Lys  Ile  His  Glu  Leu  Thr  His  Ile
               1125                1130                     1135
Asp  Tyr  Trp  Phe  Leu  His  Lys  Phe  Tyr  Asn  Ile  Tyr  Asn  Leu  Gln  Asn
               1140                1145                1150
Lys  Leu  Lys  Thr  Leu  Lys  Leu  Glu  Gln  Leu  Ser  Phe  Asn  Asp  Leu  Lys
               1155                1160                1165
Tyr  Phe  Lys  Lys  His  Gly  Phe  Ser  Asp  Lys  Gln  Ile  Ala  His  Tyr  Leu
     1170                1175                1180
Ser  Phe  Asn  Thr  Ser  Asp  Asn  Asn  Asn  Asn  Asn  Asn  Ile  Ser  Ser
1185                1190                1195                          1200
Cys  Arg  Val  Thr  Glu  Asn  Asp  Val  Met  Lys  Tyr  Arg  Glu  Lys  Leu  Gly
               1205                1210                1215
Leu  Phe  Pro  His  Ile  Lys  Val  Ile  Asp  Thr  Leu  Ser  Ala  Glu  Phe  Pro
```

|        |     |     |     |     | 1220 |     |     |     |     | 1225 |     |     |     |     | 1230 |
|--------|-----|-----|-----|-----|------|-----|-----|-----|-----|------|-----|-----|-----|-----|------|

```
        Ala   Leu   Thr   Asn   Tyr   Leu   Tyr   Leu   Thr   Tyr   Gln   Gly   Gln   Glu   His   Asp
              1235                          1240                                1245

Val   Leu   Pro   Leu   Asn   Met   Lys   Arg   Lys   Lys   Ile   Cys   Thr   Leu   Asn   Asn
              1250                          1255                                1260

Lys   Arg   Asn   Ala   Asn   Lys   Lys   Val   His   Val   Lys   Asn   His   Leu   Tyr
  1265                    1270                          1275                                1280

Asn   Glu   Val   Val   Asp   Asp   Lys   Asp   Thr   Gln   Leu   His   Lys   Glu   Asn   Asn
                                1285                          1290                          1295

Asn   Asn   Asn   Asn   Met   Asn   Ser   Gly   Asn   Val   Glu   Asn   Lys   Cys   Lys   Leu
                                1300                          1305                          1310

Asn   Lys   Glu   Ser   Tyr   Gly   Tyr   Asn   Asn   Ser   Ser   Asn   Cys   Ile   Asn   Thr
                    1315                          1320                          1325

Asn   Asn   Ile   Asn   Ile   Glu   Asn   Asn   Ile   Cys   His   Asp   Ile   Ser   Ile   Asn
                    1330                          1335                          1340

Lys   Asn   Ile   Lys   Val   Thr   Ile   Asn   Asn   Ser   Asn   Ser   Ile   Ser   Asn
  1345                    1350                          1355                                1360

Asn   Glu   Asn   Val   Glu   Thr   Asn   Leu   Asn   Cys   Val   Ser   Glu   Arg   Ala   Gly
                                1365                          1370                          1375

Ser   His   His   Ile   Tyr   Gly   Lys   Glu   Glu   Lys   Ser   Ile   Gly   Ser   Asp   Asp
                          1380                          1385                          1390

Thr   Asn   Ile   Leu   Ser   Ala   Gln   Asn   Ser   Asn   Asn   Asn   Phe   Ser   Cys   Asn
                    1395                          1400                          1405

Asn   Glu   Asn   Met   Asn   Lys   Ala   Asn   Val   Asp   Val   Asn   Val   Leu   Glu   Asn
                          1410                          1415                          1420

Asp   Thr   Lys   Lys   Arg   Glu   Asp   Ile   Asn   Thr   Thr   Thr   Val   Phe   Met   Glu
  1425                    1430                          1435                                1440

Gly   Gln   Asn   Ser   Val   Ile   Asn   Asn   Lys   Asn   Lys   Glu   Asn   Ser   Ser   Leu
                                1445                          1450                          1455

Leu   Lys   Gly   Asp   Glu   Glu   Asp   Ile   Val   Met   Val   Asn   Leu   Lys   Lys   Glu
                          1460                          1465                          1470

Asn   Asn   Tyr   Asn   Ser   Val   Ile   Asn   Asn   Val   Asp   Cys   Arg   Lys   Lys   Asp
                    1475                          1480                          1485

Met   Asp   Gly   Lys   Asn   Ile   Asn   Asp   Glu   Cys   Lys   Thr   Tyr   Lys   Lys   Asn
              1490                          1495                                1500

Lys   Tyr   Lys   Asp   Met   Gly   Leu   Asn   Asn   Asn   Ile   Val   Asp   Glu   Leu   Ser
  1505                    1510                          1515                                1520

Asn   Gly   Thr   Ser   His   Ser   Thr   Asn   Asp   His   Leu   Tyr   Leu   Asp   Asn   Phe
                                1525                          1530                          1535

Asn   Thr   Ser   Asp   Glu   Glu   Ile   Gly   Asn   Asn   Lys   Asn   Met   Asp   Met   Tyr
                          1540                          1545                          1550

Leu   Ser   Lys   Glu   Lys   Ser   Ile   Ser   Asn   Lys   Asn   Pro   Gly   Asn   Ser   Tyr
                          1555                          1560                          1565

Tyr   Val   Val   Asp   Ser   Val   Tyr   Asn   Asn   Glu   Tyr   Lys   Ile   Asn   Lys   Met
              1570                          1575                                1580

Lys   Glu   Leu   Ile   Asp   Asn   Glu   Asn   Leu   Asn   Asp   Glu   Tyr   Asn   Asn   Asn
  1585                    1590                          1595                                1600

Val   Asn   Met   Asn   Cys   Ser   Asn   Tyr   Asn   Asn   Ala   Ser   Ala   Phe   Val   Asn
                                1605                          1610                          1615

Gly   Lys   Asp   Arg   Asn   Asp   Asn   Leu   Glu   Asn   Asp   Cys   Ile   Glu   Lys   Asn
                          1620                          1625                          1630

Met   Asp   His   Thr   Tyr   Lys   His   Tyr   Asn   Arg   Leu   Asn   Asn   Arg   Arg   Ser
              1635                          1640                                1645
```

```
Thr Asn Glu Arg Met Met Leu Met Val Asn Asn Glu Lys Glu Ser Asn
1650                    1655                1660

His Glu Lys Gly His Arg Arg Asn Gly Leu Asn Lys Lys Asn Lys Glu
1665                    1670                1675                1680

Lys Asn Met Glu Lys Asn Lys Gly Lys Asn Lys Asp Lys Lys Asn Tyr
                1685                1690                1695

His Tyr Val Asn His Lys Arg Asn Asn Glu Tyr Asn Ser Asn Asn Ile
            1700                1705                1710

Glu Ser Lys Phe Asn Asn Tyr Val Asp Asp Ile Asn Lys Lys Glu Tyr
        1715                1720                1725

Tyr Glu Asp Glu Asn Asp Ile Tyr Tyr Phe Thr His Ser Ser Gln Gly
    1730                1735                1740

Asn Asn Asp Asp Leu Ser Asn Asp Asn Tyr Leu Ser Ser Glu Glu Leu
1745                1750                1755                1760

Asn Thr Asp Glu Tyr Asp Asp Asp Tyr Tyr Tyr Asp Glu Asp Glu Glu
                1765                1770                1775

Asp Asp Tyr Asp Asp Asp Asn Asp Asp Asp Asp Asp Asp Asp Asp Asp
            1780                1785                1790

Gly Glu Asp Glu Glu Asp Asn Asp Tyr Tyr Asn Asp Asp Gly Tyr Asp
                1795                1800                1805

Ser Tyr Asn Ser Leu Ser Ser Ser Arg Ile Ser Asp Val Ser Ser Val
        1810                1815                1820

Ile Tyr Ser Gly Asn Glu Asn Ile Phe Asn Glu Lys Tyr Asn Asp Ile
1825                1830                1835                1840

Gly Phe Lys Ile Ile Asp Asn Arg Asn Glu Lys Glu Lys Glu Lys Lys
                1845                1850                1855

Lys Cys Phe Ile Val Leu Gly Cys Gly Cys Tyr Arg Ile Gly Ser Ser
            1860                1865                1870

Val Glu Phe Asp Trp Ser Ala Ile His Cys Val Lys Thr Ile Arg Lys
        1875                1880                1885

Leu Asn His Lys Ala Ile Leu Ile Asn Cys Asn Pro Glu Thr Val Ser
    1890                1895                1900

Thr Asp Tyr Asp Glu Ser Asp Arg Leu Tyr Phe Asp Glu Ile Thr Thr
1905                1910                1915                1920

Glu Val Ile Lys Phe Ile Tyr Asn Phe Glu Asn Ser Asn Gly Val Ile
                1925                1930                1935

Ile Ala Phe Gly Gly Gln Thr Ser Asn Asn Leu Val Phe Ser Leu Tyr
            1940                1945                1950

Lys Asn Asn Val Asn Ile Leu Gly Ser Val His Lys Val Leu Ile Val
        1955                1960                1965

Val Lys Ile Gly Ile Asn Phe Arg Thr Tyr Val Ile Leu Lys Ile Asp
    1970                1975                1980

Gln Pro Lys Trp Asn Lys Phe Thr Lys Leu Ser Lys Ala Ile Gln Phe
1985                1990                1995                2000

Ala Asn Glu Val Lys Phe Pro Val Leu Val Arg Pro Ser Tyr Val Leu
                2005                2010                2015

Ser Gly Ala Ala Met Arg Val Val Asn Cys Phe Glu Glu Leu Lys Asn
            2020                2025                2030

Phe Leu Met Lys Ala Ala Ile Val Ser Lys Asp Asn Pro Val Val Ile
        2035                2040                2045

Ser Lys Phe Ile Glu Asn Ala Lys Glu Ile Glu Ile Asp Cys Val Ser
        2050                2055                2060

Lys Asn Gly Lys Ile Ile Asn Tyr Ala Ile Ser Glu His Val Glu Asn
2065                2070                2075                2080
```

-continued

| | | | | | | | | | | | | | | | |
|---|---|---|---|---|---|---|---|---|---|---|---|---|---|---|---|
| Ala | Gly | Val | His | Ser | Gly | Asp | Ala | Thr | Leu | Ile | Leu | Pro | Ala | Gln | Asn |
| | | | | 2085 | | | | | 2090 | | | | | 2095 | |
| Ile | Tyr | Val | Glu | Thr | His | Arg | Lys | Ile | Lys | Lys | Ile | Ser | Glu | Lys | Ile |
| | | | 2100 | | | | | 2105 | | | | | 2110 | | |
| Ser | Lys | Ser | Leu | Asn | Ile | Ser | Gly | Pro | Phe | Asn | Ile | Gln | Phe | Ile | Cys |
| | | 2115 | | | | | 2120 | | | | | 2125 | | | |
| His | Gln | Asn | Glu | Ile | Lys | Ile | Ile | Glu | Cys | Asn | Leu | Arg | Ala | Ser | Arg |
| | 2130 | | | | | 2135 | | | | | 2140 | | | | |
| Thr | Phe | Pro | Phe | Ile | Ser | Lys | Ala | Leu | Asn | Leu | Asn | Phe | Ile | Asp | Leu |
| 2145 | | | | | 2150 | | | | | 2155 | | | | | 2160 |
| Ala | Thr | Arg | Ile | Leu | Met | Gly | Tyr | Asp | Val | Lys | Pro | Ile | Asn | Ile | Ser |
| | | | | 2165 | | | | | 2170 | | | | | 2175 | |
| Leu | Ile | Asp | Leu | Glu | Tyr | Thr | Ala | Val | Lys | Ala | Pro | Ile | Phe | Ser | Phe |
| | | | 2180 | | | | | 2185 | | | | | 2190 | | |
| Asn | Arg | Leu | His | Gly | Ser | Asp | Cys | Ile | Leu | Gly | Val | Glu | Met | Lys | Ser |
| | | 2195 | | | | | 2200 | | | | | 2205 | | | |
| Thr | Gly | Glu | Val | Ala | Cys | Phe | Gly | Leu | Asn | Lys | Tyr | Glu | Ala | Leu | Leu |
| | 2210 | | | | | 2215 | | | | | 2220 | | | | |
| Lys | Ser | Leu | Ile | Ala | Thr | Gly | Met | Lys | Leu | Pro | Lys | Lys | Ser | Ile | Leu |
| 2225 | | | | | 2230 | | | | | 2235 | | | | | 2240 |
| Ile | Ser | Ile | Lys | Asn | Leu | Asn | Asn | Lys | Leu | Ala | Phe | Glu | Glu | Pro | Phe |
| | | | | 2245 | | | | | 2250 | | | | | 2255 | |
| Gln | Leu | Leu | Phe | Leu | Met | Gly | Phe | Thr | Ile | Tyr | Ala | Thr | Glu | Gly | Thr |
| | | | 2260 | | | | | 2265 | | | | | 2270 | | |
| Tyr | Asp | Phe | Tyr | Ser | Lys | Phe | Leu | Glu | Ser | Phe | Asn | Val | Asn | Lys | Gly |
| | | 2275 | | | | | 2280 | | | | | 2285 | | | |
| Ser | Lys | Phe | His | Gln | Arg | Leu | Ile | Lys | Val | His | Asn | Lys | Asn | Ala | Glu |
| | 2290 | | | | | 2295 | | | | | 2300 | | | | |
| Asn | Ile | Ser | Pro | Asn | Thr | Thr | Asp | Leu | Ile | Met | Asn | His | Lys | Val | Glu |
| 2305 | | | | | 2310 | | | | | 2315 | | | | | 2320 |
| Met | Val | Ile | Asn | Ile | Thr | Asp | Thr | Leu | Lys | Thr | Lys | Val | Ser | Ser | Asn |
| | | | | 2325 | | | | | 2330 | | | | | 2335 | |
| Gly | Tyr | Lys | Ile | Arg | Arg | Leu | Ala | Ser | Asp | Phe | Gln | Val | Pro | Leu | Ile |
| | | | 2340 | | | | | 2345 | | | | | 2350 | | |
| Thr | Asn | Met | Lys | Leu | Cys | Ser | Leu | Phe | Ile | Asp | Ser | Leu | Tyr | Arg | Lys |
| | | 2355 | | | | | 2360 | | | | | 2365 | | | |
| Phe | Ser | Arg | Gln | Lys | Glu | Arg | Lys | Ser | Phe | Tyr | Thr | Ile | Lys | Ser | Tyr |
| | 2370 | | | | | 2375 | | | | | 2380 | | | | |
| Asp | Glu | Tyr | Ile | Ser | Leu | Val | | | | | | | | | |
| 2385 | | | | | 2390 | | | | | | | | | | |

NUCLEOTIDE SEQUENCE ENCODING CARBAMOYL PHOSPHATE SYNTHETASE II

This is a national phase filing of PCT application PCT/AU93/00617, filed Dec. 2, 1993.

The present invention relates to nucleotide sequences encoding carbamoyl phosphate synthetase II of *Plasmodium falciparum*, to methods of producing this enzyme using recombinant DNA technology and to the use of this sequence and enzyme in the design of therapeutics.

BACKGROUND OF THE INVENTION

The urgency for the design of novel chemotherapeutic agents for the treatment of malaria has been renewed in recent times due to the evolution of human malarial parasites, primarily *Plasmodium falciparum*, which are resistant to traditional drugs. Research into a vaccine seems a very plausible alternative, but after years of investigation, no clinically acceptable product has come to date. At the same time, there is also an increasing decline in the efficacy of insecticides against mosquito vectors. At present, more than two-thirds of the world's population—approximately 500 million people—are thought to live in malaria areas (Miller, 1989). It ranks eighth in the World Health Organization's (WHO) list of ten most prevalent diseases of the world (270 million infections a year) and ranks ninth of the ten most deadly diseases, claiming over 2 million lives a year (Cox, 1991; Marshall, 1991). Though chiefly confined to poor nations, there are recent reports of infections in the United States (Marshall, 1991) and Australia (Johnson, 1991), and ever increasing cases of travellers' malaria (Steffen and Behrens, 1992).

Comparative biochemical studies between the malaria parasite, *P. falciparum* and its host have revealed differences in a number of metabolic pathways. One such distinction is that the parasite relies exclusively on pyrimidine synthesis de novo because of its inability to salvage preformed pyrimidines (Sherman, 1979). Moreover, the mature human red blood cell has no recognised requirement for pyrimidine nucleotides (Gero and O'Sullivan, 1990). Major efforts have been directed towards the development of inhibitors of the pyrimidine biosynthetic pathway (Hammond et al., 1985; Scott et al., 1986; Prapunwattana et al., 1988; Queen et al., 1990; Krungkrai et al., 1992), confirming its potential as a chemotherapeutic locus. Current research into the molecular biology of the key pyrimidine enzymes is envisioned as a powerful tool, not only to get a better understanding of the parasite's biochemistry, but also to explore specific differences between the parasite and the mammalian enzymes.

Glutamine-dependent carbamoyl phosphate synthetase (CPSII, EC 6.3.5.5) catalyses the first committed and rate-limiting step in the de novo pyrimidine biosynthetic pathway of eukaryotic organisms (Jones, 1980). Moreover, because it catalyzes a complex reaction involving three catalytic units and several substrates and intermediates, it is a very interesting enzyme to study from a biochemical point of view. The structural relationship of CPSII to other pyrimidine enzymes varies in different organisms, making it a good subject for evolutionary studies.

The paucity of material that can be obtained from malarial cultures has hampered the isolation of adequate amounts of pure protein for analysis. The difficulty in purifying CPS is further augmented by its inherent instability. Studies using crude extracts from *P. berghei* (a rodent malaria) revealed a high molecular weight protein containing CPS activity, which was assumed to be associated with ATCase (Hill et al., 1981), a situation also found in yeast (Makoff and Radford, 1978). However, recent analysis by Krungkrai and co-workers (1990) detected separate CPSII and ATCase activities in *P. berghei*. Although CPS activity has been detected in *P. falciparum* (Reyes et al., 1982) until this current study there is no indication of its size nor its linkage with other enzymes in the pathway.

The glutamine-dependent activity of CPSII can be divided into two steps: (1) a glutaminase (GLNase) reaction which hydrolyzes glutamine (Gln) and transfers ammonia to the site of the carbamoyl phosphate synthetase; and (2) a synthetase reaction where carbamoyl phosphate is synthesised from two molecules of adenosine triphosphate (ATP), bicarbonate and ammonia. The second activity involves three partial reactions: (a) the activation of bicarbonate by ATP; (b) the reaction of the activated species carboxyphosphate with ammonia to form carbamate; and (c) the ATP-dependent phosphorylation of carbamate to form carbamoyl phosphate (powers and Meister, 1978). Hence, there are two major domains in CPSII, the glutamine amidotransferase domain (GAT) and the carbamoyl phosphate synthetase domain (CPS) or simply synthetase domain. The glutaminase domain (GLNase) is a subdomain of GAT, while there are two ATP-binding subdomains in the synthetase domain.

In view of the similarities between the glutamine amidotransferase domain of CPS and other amidotransferases, it has been proposed that these subunits arose by divergent evolution from a common ancestral gene (≈20 kDa) representing the GLNase domain and that particular evolution of the CPS GAT domain (≈42 kDa which includes the putative structural domain only present in CPS) must have involved fusions and/or insertions of other sequences (Werner et al., 1985). The GAT of mammalian CPSI gene has been proposed to be formed by a simple gene fusion event at the 5' end of this ancestral gene with an unknown gene (Nyunoya et al., 1985).

The genes for the larger synthetase domains of various organisms were postulated to have undergone a gene duplication of an ancestral kinase gene resulting in a polypeptide with two homologous halves (Simmer et al., 1990). Unlike the subunit structure of *E. coli* and arginine-specific CPS of yeast, a further fusion of the genes encoding GAT and the synthetase domains was suggested to have formed the single gene specific for pyrimidine biosynthesis in higher eukaryotes. Conversely, Simmer and colleagues (1990) proposed that the arginine-specific CPS's (like cpa1 and cpa2 in yeast) as well as rate mitochondrial CPSI arose by defusion from the pyrimidine chimera.

DESCRIPTION OF THE INVENTION

The present inventors have isolated and characterised the complete gene encoding the CPSII enzyme from *P. falciparum* (pfCPSII). Reported here is the sequence including 5' and 3' untranslated regions. In so doing, the present inventors have identified the respective glutaminase and synthetase domains. Unlike CPSII genes in yeast, *D. discoideum*, and mammals, there is no evidence for linkage to the subsequent enzyme, aspartate transcarbamoylase (ATCase). This is in contrast to the report by Hill et al., (1981) for the enzymes from *P. berghei*. The present inventors have, however, found two large inserts in the *P. falciparum* gene of a nature that does not appear to have been previously described.

Accordingly, in a first aspect, the present invention consists in a nucleic acid molecule encoding carbamoyl phosphate synthetase II of *Plasmodium falciparum*, the nucleic acid molecule including a sequence substantially as shown in Table 1 from 1 to 7176, or from 1 to 750, or from 751 to 1446, or from 1447 to 2070, or from 2071 to 3762, or from 3763 to 5571, or from 5572 to 7173, or from 1 to 3360, or from 2071 to 6666, or from 2071 to 7173, or a functionally equivalent sequence.

In a preferred embodiment of the present invention, the nucleic acid molecule includes a sequence shown in Table 1 from −1225 to 7695 or a functionally equivalent sequence.

In a second aspect, the present invention consists in an isolated polypeptide, the polypeptide including an amino acid sequence substantially as shown in Table 1 from 1 to 2391, from 483 to 690, from 691 to 1254, 1858 to 2391, from 1 to 1120, from 691 to 2222, or from 691 to 2391.

As used herein the term "functionally equivalent sequence" is intended to cover minor variations in the nucleic acid sequence which, due to degeneracy in the code, do not result in the sequence encoding a different polypeptide.

In a third aspect the present invention consists in a method of producing *Plasmodium falciparum* carbamoyl phosphate synthetase II, the method comprising culturing a cell transformed with the nucleic acid molecule of the first aspect of the present invention under conditions which allow expression of the nucleic acid sequence, and recovering the expressed carbamoyl phosphate synthetase II.

The cells may be either bacteria or eukaryotic cells. Examples of preferred cells include *E. coli*, yeast, and *Dictyostelium discoideum*.

As will be readily understood by persons skilled in this field, the elucidation of the nucleotide sequence for CPSII enables the production of a range of therapeutic agents. These include antisense nucleotides, ribozymes, and the targeting of RNA and DNA sequences using other approaches, e.g., triplex formation.

As can be seen from a consideration of the sequence set out in Table 1 the *Plasmodium falciparum* CPSII gene includes two inserted sequences not found in other carbamoyl phosphate synthetase genes. The first inserted sequence separates the putative structural domain and the glutiminase domain whilst the second inserted sequence separates the two ATP binding subdomains of the synthetase subunit CPSa and CPSb.

TABLE 1

Nucleotide and Deduced Amino Acid Sequence of the
Carbamoyl Phosphate Synthetase II Gene from *Plasmodium falciparum* (SEQ ID NOS: 1 and 2)

```
-1225  GAATTCCTTCAGCCAAAAAAAATGACAACGCAAATTTTAAGAAAAGAAAAACAATCGACT  -1166

-1165  CGTCTTTGAATGAGGTTAGAAATTCGATACGTGAAAGGGACTTAAGAAGGCTTAACAGAG  -1106

-1105  AAAAGAGTAAAATCTTATAAGCATTTGAAGGAAAAAATAATAAAATAAAAAAATAAAAAG  -1046

-1045  ATAAAAAATATTTATATTTGATATGTAGTATATATAATGATTATTCATATTAATAACATA   -986

-985  GATAAAAAACTTTTTTTTTTTTTTTTTCTTTATATTTATTAACAATACATTTAAGTTA    -926

-925  TTTTATATATATATATATATATATATATATATATATATATATGTTTGTGTGTTCAT      -866

-865  TTGTTTATAAAATTACTTGAAATATAAAACTTATTAATATATTTCCAATTAATATGAATA  -806

-805  CAATTATTAATATTTTGATGTGTACACATTAATATAGTTTTACACTTCTTATAATAAAAC  -746

-745  CATCCTATATATTATACACAATATATAATACTCCCCAATATTGTGGTTCCTATAATTTTA  -686

-685  TTTATATATTTATTTATTAATTTATTCATTTATTTATTTTTTTCTTAGTTTATAAAATA   -626

-625  GTAATTCTACTAATTTAAAAAAAAAAAAAAAAAAAAAAAAAAAAAAGAAAAAAAAAAAATT -566

-565  TACATATGAAAAATGAACTTGTATATGTAAATTTATAAATATTTTAAACATAAATATAAA  -506

-505  TGTATAAAAAAAAAAAAGAAAAATGGGAAAAAATAATATAGATATATATATAAATATATA  -446

-445  TATATATATAATTATTGGGGATATTCTCTGAATCATAGGTCTTAAACAGTTTTATTCTTT  -386

-385  TAACATGACAAAGTTGTTATTAAAAGTATATATATCTTATTGGTTCCTATATAAAACTAT  -326

-325  AGTATTCTATAATATATTCTGTATATTTCATTTTATCATTTGTAAGCAATCCCTATTTAT  -266
```

TABLE 1-continued

Nucleotide and Deduced Amino Acid Sequence of the
Carbamoyl Phosphate Synthetase II Gene from *Plasmodium
falciparum* (SEQ ID NOS: 1 and 2)

```
-265 TATAATTATTATTTTTTTTTTATAAAAGAGGTATAAAACAGTTTATTCAATTTTTTCC  -206

-205 TAAAGGAGCAACCTTCAGTCAATTTACATTTTCCACCGGTTGGTTGGCACAACATAATGT -146

-145 TACAGCTAAAAAAAGAAAGAAAAAAAAAAAAAAAAAAAAAAAAAAAAAAAAAATATATATAT -86

-85 ATATATATATATATACATAATATGTACAATGCTACCATACAAGTATATAAATTTTTCAAC -26

-25 ATTGTTGTGATGTTGCATTTTTCTT                                     -1
```

```
  1 ATGTATATTTCTTTTAAATATAATTTATATATATATATATATATATATATATATATATTT  60
  1 M   Y   I   S   F   K   Y   N   L   Y   I   Y   I   Y   I   Y   I   Y   I   F    20

61 GTTCTTATAGATTTTAAAAGAGTTGGGAGGTTAATTCTTGAAGATGGTAACGAATTTGTA 120
 21 V   L   I   D   F   K   T   V   G   R   L   I   L   E   D   G   N   E   F   V    40

121 GGGTACAGTGTAGGTTACGAAGGGTGTAAAGGAAATAATAGTATATCATGTCATAAGGAG 180
 41 G   Y   S   V   G   Y   E   G   C   K   G   N   N   S   I   S   C   H   K   E    60

181 TATAGAAATATTATTAATAATGATAATAGCAAGAATAGTAATAATTCATTTTGTAATAAT 240
 61 Y   R   N   I   I   H   N   D   N   S   K   N   S   N   N   S   F   C   N   N    80

241 GAAGAAAACAATTTGAAAGATGATTTATTATATAAAAATAGTCGATTAGAAAATGAAGAT 300
 81 E   E   N   N   L   K   D   D   L   L   Y   K   N   S   R   L   E   N   E   D   100

301 TTTATTGTTACAGGTGAAGTTATATTTAATACAGCTATGGTTGGATATCCTGAAGCTTTA 360
101 F   I   V   T   G   E   V   I   F   N   T   A   M   V   G   Y   P   E   A   L   120

361 ACGGACCCAAGTTATTTTGGTCAAATATTAGTTTTAACATTTCCTTCTATTGGTAATTAT 420
121 T   D   P   G   Y   F   G   Q   I   L   V   L   T   F   P   S   I   G   N   Y   140

421 GGTATTGAAAAAGTAAAACATGATGAAACGTTTGGATTAGTACAAAATTTTGAAAGTAAT 480
141 G   I   E   K   V   K   H   D   E   T   F   G   L   V   Q   N   F   E   S   N   160

481 AAAATTCAAGTACAAGGTTTAGTTATTTGTGAATATTCGAAGCAATCATATCATTACAAT 540
161 K   I   Q   V   Q   G   L   V   I   C   E   Y   S   K   Q   S   Y   H   Y   N   180

541 TCTTATATTACCTTAAGTGAATGGTTAAAGATTTATAAAATTCCATGTATAGGTGGTATA 600
181 S   Y   I   T   L   S   E   W   L   K   I   Y   K   I   F   C   I   G   G   I   200

601 GATACAAGAGCCTTAACAAAACTTTTAAGAGAAAAAGGTAGTATGTTAGGTAAAATAGTT 660
201 D   T   R   A   L   T   K   L   L   R   E   K   G   S   M   L   G   K   I   V   220

661 ATATATAAAAACAGACAACATATTAATAAATTATATAAAGAAATTAATCTTTTTGATCCT 720
221 I   Y   K   N   R   Q   H   I   N   K   L   Y   K   E   I   N   L   F   D   F   240

721 GGTAATATAGATACTCTAAAATATGTATGTAATCATTTTATACGTGTTATTAAGTTGAAT 780
241 G   N   I   D   T   L   K   Y   V   C   N   H   F   I   R   V   I   K   L   N   260

781 AATATTACATATAATTATAAAAATAAGGAAGAATTTAATTATACCAATGAAATGATTACT 840
261 N   I   T   Y   N   Y   K   N   K   E   E   F   N   Y   T   N   E   M   I   T   280

841 AATGATTCTTCAATGGAAGATCATGATAATGAAATTAATGGTAGTATTTCTAATTTTAAT 900
281 D   D   S   S   M   E   D   H   D   N   E   I   N   G   S   I   S   N   F   N   300
```

TABLE 1-continued

Nucleotide and Deduced Amino Acid Sequence of the
Carbamoyl Phosphate Synthetase II Gene from *Plasmodium falciparum* (SEQ ID NOS: 1 and 2)

```
 901 AATTGTCCAAGTATCTCTAGTTTTGATAAAAGTGAATCGAAAAATGTTATTAATCATACA  960
 301  N  C  P  S  I  S  S  F  D  K  S  E  S  K  N  V  I  N  H  T     320

961 TTGTTAAGAGATAAAATGAACCTAATAACTTCATCTGAAGAATATCTGAAAGATCTTCAT 1020
 321  L  L  R  D  K  M  W  L  I  T  S  S  E  E  Y  L  K  D  L  H     340

1021 AATTGTAATTTTAGTAATAGTAGTGATAAAAATGATTCTTTTTTTAAGTTATATGGTATA 1080
 341  N  C  N  F  S  N  S  S  D  K  N  D  S  F  F  K  L  Y  G  I     360

1081 TGTGAATATGATAAATATTTAATTGACCTTGAAGAAAATGCTAGCTTTCATTATAATAAT 1140
 361  C  E  Y  D  K  Y  L  I  D  L  E  E  N  A  S  F  H  Y  N  N     380

1141 GTAGATGAATATGGATATTATGATGTTAATAAAAATACAAATATTCTATCTAATAATAAA 1200
 381  V  D  E  Y  G  Y  Y  D  V  N  K  N  T  N  I  L  S  N  N  K     400

1201 ATAGAACAAAACAACAATAACGAAAATAACAAAAATAACAAAAATAACAACAATAACGAG 1260
 401  I  E  Q  N  N  N  N  E  N  N  K  N  N  K  N  N  N  N  N  E     420

1261 GTTGATTATATAAAGAAAGATGAGGATAATAATGTCAATAGTAAGGTCTTTTATAGCCAA 1320
 421  V  D  Y  I  K  K  D  E  D  N  N  V  N  S  K  V  F  Y  S  Q     440

1321 TATAATAATAATGCACAAAATAATGAACATACCGAATTTAATTTAAATAATGATTATTCT 1380
 441  Y  N  N  N  A  Q  N  N  E  H  T  E  F  N  L  N  N  D  Y  S     460

1381 ACTTATATTAGAAAGAAAATGAAAAATGAAGAATTCCTTAATTTGGTAAACAAAAGAAAA 1440
 461  T  Y  I  R  K  K  M  K  N  E  E  F  L  N  L  V  N  K  R  K     480

1441 GTAGACCATAAAGAAAAAATTATTGTTATTGTTGATTGTGGTATTAAAAATAGTATAATC 1500
 481  V  D  H  K  E  K  I  I  V  I  V  D  C  G  I  K  N  S  I  I     500

1501 AAAAATTTAATAAGACACGGTATGGATCTTCCATTAACATATATTATTGTACCTTATTAT 1560
 501  K  N  L  I  R  H  G  M  D  L  P  L  T  Y  I  I  V  P  Y  Y     529

1561 TACAATTTTAATGATATAGATTATGATGCAGTTCTTTTATCTAATGGTCCTGGAGATCCT 1620
 521  Y  N  F  N  H  I  D  Y  D  A  V  L  L  S  N  G  P  G  D  P     540

1621 AAAAAGTGTGATTTCCTTATAAAAAATTTGAAAGATAGTTTAACAAAAAATAAAATTATA 1680
 541  K  K  C  D  F  L  I  K  N  L  K  D  S  L  T  K  N  K  I  I     560

1681 TTTGGTATTTGTTTAGGTAATCAACTATTAGGTATATCATTAGGTTGTGACACATATAAA 1740
 561  F  G  I  C  L  G  N  Q  L  L  G  I  S  L  G  C  D  T  Y  K     580

1741 ATGAAATATGGTAATAGAGGTGTTAATCAACCCGTAATACAATTAGTAGATAATATATGT 1800
 581  M  K  Y  G  N  E  G  V  N  Q  P  V  I  Q  L  V  D  N  I  C     600

1801 TACATTACCTCACAAAATCATGGATACTGTTTAAAGAAAAAATCAATTTTAAAAAGAAAA 1860
 601  Y  I  T  S  Q  N  H  G  Y  C  L  K  K  K  S  I  L  K  H  K     620

1861 GAGCTTGCGATTAGTTATATAAATGGTAATGATAAATCTATAGAAGGTATTTCACATAAA 1920
 621  E  L  A  I  S  Y  I  N  A  N  D  K  S  I  E  G  I  S  H  K     640

1921 AATGGAAGATTTTATAGTGTCCAGTTTCATCCTGAGGGTAATAATGGTCCTGAAGATACA 1980
 641  N  G  R  F  Y  S  V  Q  F  H  P  E  G  N  N  G  P  E  D  T     660

1981 TCATTTTTATTTAAGAATTTTCTTTTAGATATCTTTAATAAGAAAAAACAATATAGAGAA 2040
 661  S  F  L  F  K  N  F  L  L  D  I  F  N  K  K  Q  Y  R  E        680
```

TABLE 1-continued

Nucleotide and Deduced Amino Acid Sequence of the
Carbamoyl Phosphate Synthetase II Gene from *Plasmodium falciparum* (SEQ ID NOS: 1 and 2)

```
2041 TATTTAGGATATAATATTATTTATATAAAAAAGAAAGTGCTTCTTTTAGGTAGTGGTGGT 2100
 681 Y   L   G   Y   N   I   I   Y   I   K   K   K   V   L   L   G   S   G   G    700

2101 TTATGTATAGGACAAGCAGGAGAATTCGATTATTCAGGAACACAAGCAATTAAAAGTTTA 2160
 701 L   C   I   G   Q   A   G   K   F   D   Y   S   G   I   Q   A   I   K   S   L  720

2161 AAAGAATGTGGTATATATGTTATATTAGTTAATCCTAACATAGCAACTGTTCAAACATGA 2220
 721 K   E   C   G   I   Y   V   I   L   V   N   P   N   I   A   T   V   Q   T   S  740

2221 AAAGGTTTGGCAGATAAGGTATACTTTTTACCAGTTAATTGTGAATTTGTAGAAAAAATT 2280
 741 K   G   L   A   D   K   V   Y   F   L   P   V   N   C   E   F   V   E   K   I  760

2281 ATTAAAAAGGAAAAACCTGATTTTATTTTATGTACATTTGGTGGTCAGACAGCTTTAAAT 2340
 761 I   K   K   E   K   P   D   F   I   L   C   T   F   G   G   Q   T   A   L   N  780

2341 TGTGCTTTAATGTTAGATCAAAAAAAAGTATTGAAAAAGAATAATTGTCAATGTTTAGGT 2400
 781 C   A   L   M   L   D   Q   K   K   V   L   K   K   N   N   C   Q   C   L   G  800

2401 ACATCTTTAGAATCTATAAGAATAACAGAAAATAGAACATTATTTGCTGAAAAATTAAAA 2460
 801 T   S   L   E   S   I   R   I   T   E   N   R   T   L   F   A   E   K   L   K  820

2461 GAAATTAATGAAAGAATAGCTCCATATGGTAGTGCAAAAAATGTTAATCAAGCTATTGAT 2520
 821 E   I   N   E   R   I   A   F   Y   G   S   A   K   N   V   N   Q   A   I   D  840

2521 ATAGCTAATAAAATAGGATATCCAATATTAGTACGTACAACATTTTCGTTAGGAGGATTA 2580
 841 I   A   N   K   I   G   Y   F   I   L   V   R   T   T   F   S   L   G   G   L  860

2581 AATAGTAGTTTCATAAATAATGAAGAAGAACTTATCGAAAAATGTAATAAAATATTTTTA 2640
 861 N   S   S   F   I   N   N   E   E   E   L   I   E   K   C   N   K   I   F   L  880

2641 CAAACTGATAATGAAATATTTATAGATAAATCATTACAAGGATGGAAAGAAATAGAATAT 2700
 881 Q   T   D   N   E   I   F   I   D   K   S   L   Q   G   W   K   E   I   E   Y  900

2701 GAATTATTAAGAGATAATAAAAATAATTGTATAGCTATATGTAATATGGAAAATATAGAT 2760
 901 E   L   L   R   D   N   K   N   N   C   I   A   I   C   N   M   E   N   I   D  920

2761 CCATTAGGTATACATACAGGAGATAGTATAGTTGTTGCACCTTCACAAACATTAAGTAAT 2820
 921 P   L   G   I   H   T   G   D   S   I   V   V   A   P   S   Q   T   L   S   N  940

2821 TATGAATATTATAAATTTAGAGAAATAGCATTAAAGGTAATTACACATTTAAATATTATA 2880
 941 Y   E   Y   Y   K   F   R   E   I   A   L   K   V   I   T   H   L   N   I   I  960

2881 GGAGAATGTAATATACAATTTGGTATAAATCCACAAACAGGAGAATATTGTATTATTGAA 2940
 961 G   E   C   N   I   Q   F   G   I   N   P   Q   T   G   E   Y   C   I   I   E  980

2941 GTTAATGCTAGGCTTAGTAGAAGTTCAGCATTAGCTTCTAAAGCTACTGGTTATCCACTT 3000
 981 V   N   A   R   L   S   R   S   S   A   L   A   S   K   A   T   G   Y   P   L 1000

3001 GCTTATATATCAGCAAAAATAGCCTTGGGATATGATTTGATAAGTTTAAAAAATAGCATA 3060
1001 A   Y   I   S   A   K   I   A   L   G   Y   D   L   I   S   L   K   N   S   I 1020

3061 ACTAAAAAAACAACTGCCTGTTTTGAACCCTCTCTAGATTACATTACAACAAAAATACCA 3120
1021 T   K   K   T   T   A   C   F   E   F   S   L   D   Y   I   T   T   K   I   P 1040

3121 CGATGGGATTTAAATAAATTTGAGTTTGCTTCTAATACAATGAATAGTAGTATGAAAAGT 3180
1041 R   W   D   L   N   K   F   E   F   A   S   N   T   M   N   S   S   M   K   S 1060
```

TABLE 1-continued

Nucleotide and Deduced Amino Acid Sequence of the
Carbamoyl Phosphate Synthetase II Gene from *Plasmodium falciparum* (SEQ ID NOS: 1 and 2)

```
3181 GTAGGAGAAGTTATGTCTATAGGTAGAACCTTTGAAGAATCTATACAAAAATCTTTAAGA 3240
1061  V  G  E  V  M  S  I  G  R  T  F  E  E  S  I  Q  K  S  L  R  1080

3241 TGTATTGATGATAATTATTTAGGATTTAGTAATACGTATTGTATAGATTGGGATGAAAAG 3300
1081  C  I  D  D  N  Y  L  G  F  S  N  T  Y  C  I  D  W  D  E  K  1100

3301 AAAATTATTGAAGAATTAAAAAATGGATCACCAAAAAGAATTGATGCTATACATCAAGCT 3360
1101  K  I  I  E  E  L  K  N  F  S  P  K  R  I  D  A  I  H  Q  A  1120

3361 TTCCATTTAAATATGCCTATGGATAAAATACATGAGCTGACACATATTGATTATTGGTTC 3420
1121  F  H  L  N  M  P  M  D  K  I  H  E  L  T  H  I  D  Y  W  F  1140

3421 TTACATAAATTTTATAATATATATAATTTAGAAAATAAGTTGAAAACGTTAAAATTAGAG 3480
1141  L  H  K  F  Y  N  I  Y  N  L  Q  N  K  L  K  I  L  K  L  E  1160

3481 CAATTATCTTTTAATGATTTGAAGTATTTTAAGAAGCATGGTTTTAGTGATAAGCAAATA 3540
1161  Q  L  S  F  N  D  L  K  Y  F  K  K  H  G  F  S  D  K  Q  I  1180

3541 GCTCACTACTTATCCTTCAACACAAGCGATAATAATAATAATAATAATAATATTAGCTCA 3600
1181  A  H  Y  L  S  F  N  T  S  D  N  N  N  N  N  N  N  I  S  S  1200

3601 TGTAGGGTTACAGAAAATGATGTTATGAAATATAGAGAAAAGCTAGGATTATTTCCACAT 3660
1201  C  R  V  T  E  N  D  V  M  K  Y  R  E  K  L  G  L  F  P  H  1220

3661 ATTAAAGTTATTGATACCTTATCAGCCGAATTTCCGGCTTTAACTAATTATTTATATTTA 3720
1221  I  K  V  I  D  T  L  S  A  E  F  P  A  L  T  N  Y  L  Y  L  1240

3721 ACTTATCAAGGTCAAGAACATGATGTTCTCCCATTAAATATGAAAAGGAAAAAGATATGC 3780
1241  T  Y  Q  G  Q  E  H  D  V  L  F  L  N  M  K  R  K  K  I  C  1260

3781 ACGCTTAATAATAAACGAAATGCAAATAAGAAAAAAGTCCATGTCAAGAACCACTTATAT 3840
1261  T  L  N  N  K  R  N  A  N  K  K  K  V  H  V  K  N  H  L  Y  1280

3841 AATGAAGTAGTTGATGATAAGGATACACAATTACACAAAGAAAATAATAATAATAATAAT 3900
1281  N  E  V  V  D  D  K  D  T  Q  L  H  K  E  N  N  N  N  N  N  1300

3901 ATGAATTCTGGAAATGTAGAAAATAAATGTAAATTGAATAAAGAATCCTATGGCTATAAT 3960
1301  M  N  S  G  N  V  E  N  K  C  K  L  N  K  E  S  Y  G  Y  N  1320

3961 AATTCTTCTAATTGTATCAATACAAATAATATTAATATAGAAAATAATATTTGTCATGAT 4020
1321  N  S  S  N  C  I  N  T  N  N  I  N  I  E  N  N  I  C  H  D  1340

4021 ATATCTATAAACAAAAATATAAAAGTTACAATAAACAATTCCAATAATTCTATATCGAAT 4080
1341  I  S  I  N  K  N  I  K  V  T  I  N  N  S  N  N  S  I  S  N  1360

4081 AATGAAAATGTTGAAACAAACTTAAATTGTGTATCTGAAAGGGCCGGTAGCCATCATATA 4140
1361  N  E  N  V  E  T  N  L  N  C  V  S  E  R  A  G  S  H  H  I  1380

4141 TATGGTAAAGAAGAAAAGAGTATAGGATCTGATGATACAAATATTTTAAGTGCACAAAAT 4300
1381  Y  G  K  E  E  K  S  I  G  S  D  D  T  N  I  L  S  A  Q  N  1400

4201 TCAAATAATAACTTTTCATGTAATAATGAGAATATGAATAAAGCAAACGTTGATGTTAAT 4260
1401  S  N  N  N  F  S  C  N  N  E  N  M  N  K  A  N  V  D  V  N  1420

4261 GTACTAGAAAATGATACGAAAAAACGAGAAGATATAAATACTACAACAGTATTTATGGAA 4320
1421  V  L  E  N  D  T  K  K  R  E  D  I  N  T  T  V  F  M  E  1440
```

TABLE 1-continued

Nucleotide and Deduced Amino Acid Sequence of the
Carbamoyl Phosphate Synthetase II Gene from *Plasmodium
falciparum* (SEQ ID NOS: 1 and 2)

```
4321 GGTCAAAATAGTGTTATTAATAATAAGAATAAAGAGAATAGTTCTTTATTGAAAGGTGAT 4380
1441  G   Q   N   S   V   I   N   N   K   N   K   E   N   S   S   L   L   K   G   D   1460

4381 GAAGAAGATATTGTGATGGTAAATTTAAAAAAGGAAAATAATTATAATAGTGTAATTAAT 4440
1461  E   E   D   I   V   M   V   N   L   K   K   E   N   N   Y   N   S   V   I   N   1480

4441 AATGTAGATTGTAGGAAAAAGGATATGGATGGAAAAAATATAAATGATGAATGTAAAACA 4500
1481  N   V   D   C   R   K   K   D   M   D   G   K   N   I   N   D   E   D   K   T   1500

4501 TATAAGAAAAATAAATATAAAGATATGGGATTAAATAATAATATAGTAGATGAGTTATCC 4560
1501  Y   K   K   N   K   Y   K   D   M   G   L   N   N   N   I   V   D   E   L   S   1520

4561 AATGGAACATGACATTCAACTAATGATCATTTATATTTAGATAATTTTAATACATCAGAT 4620
1521  N   G   T   S   H   S   T   N   D   H   L   Y   L   D   N   F   N   T   S   D   1540

4621 GAAGAAATAGGGAATAATAAAAATATGGATATGTATTTATCTAAGGAAAAAAGTATATCT 4680
1541  E   E   I   G   N   N   K   N   M   D   M   Y   L   S   K   E   K   S   I   S   1560

4681 AATAAAAACCCTGGTAATTCTTATTATGTTGTAGATTCCGTATATAATAATGAATACAAA 4740
1561  N   K   N   P   G   N   S   Y   Y   V   V   D   S   V   Y   N   N   E   Y   R   1580

4741 ATTAATAAGATGAAAGAGTTAATAGATAACTGAAAATTTAAATGATGATATAATAATAAT 4800
1581  I   N   K   M   K   E   L   I   D   N   E   N   L   N   D   E   Y   N   N   N   1600

4801 GTTAATATGAATTGTTCTAATTATAATAATGCTAGTGCATTTGTAAATGGAAAGGATAGA 4860
1601  V   N   M   N   C   S   N   Y   N   N   A   S   A   F   V   N   G   K   D   R   1620

4861 AATGATAATTTAGAAAATGATTGTATTGAAAAAAATATGGATCATACATACAAACATTAT 4920
1621  N   D   N   L   E   N   D   C   I   E   K   N   M   D   H   T   Y   K   H   Y   1640

4921 AATCGTTTAAACAATCGTAGAAGTACAAATGAGAGGATGATGCTTATGGTAAACAATGAA 4980
1641  N   R   L   N   N   R   R   S   T   N   E   R   M   M   L   M   V   N   N   E   1660

4981 AAAGAGAGCAATCATGAGAAGGGCCATAGAAGAAATGGTTTAAATAAAAAAAATAAAGAA 5040
1661  K   E   S   N   H   E   K   G   H   R   R   N   G   L   N   K   X   N   X   E   1680

5041 AAAAATATGGAAAAAAATAAGGGAAAAAATAAAGACAAAAAGAATTATCATTATGTTAAT 5100
1681  K   N   M   E   K   N   G   K   N   K   D   K   K   N   Y   H   Y   V   H   1700

5101 GATAAAAGGAATAATGAATATAATAGTAACAATATTGAATCGAAGTTTAATAATTATGTT 5160
1701  H   K   R   N   N   E   Y   N   S   N   N   I   E   S   K   F   N   N   Y   V   1720

5161 GATGATATAAATAAAAAGAATATTATGAAGATGAAATGATATATATTATTTTACACAT 5220
1721  D   D   I   N   K   K   E   Y   Y   E   D   E   N   D   I   Y   Y   F   T   H   1740

5221 TCGTCACAAGGTAACAATGACGATTTAAGTAATGATAATTATTTAAGTAGTGAAGAATTG 5280
1741  S   S   Q   G   N   N   D   D   L   S   N   D   N   Y   L   S   S   E   E   L   1760

5281 AATACTGATGAGTATGATGATGATTATTATTATGATGAAGATGAAGAAGATGACTATGAC 5340
1761  N   T   D   E   Y   D   D   D   Y   Y   Y   D   E   D   E   E   D   Y   D   1780

5341 GATGATAATGATGATGATGATGATGATGATGATGATGATGGGGAGGATGAGGAGGATAATGAT 5400
1781  D   D   N   D   D   D   D   D   D   D   D   G   E   D   E   E   D   N   D   1800

5401 TATTATAATGATGATGGTTATGATAGCTATAATTCTTTATCATCTTCAAGAATATCAGAT 5460
1801  Y   Y   N   D   D   G   Y   D   S   Y   N   S   L   S   S   S   R   I   S   D   1820
```

TABLE 1-continued

Nucleotide and Deduced Amino Acid Sequence of the Carbamoyl Phosphate Synthetase II Gene from *Plasmodium falciparum* (SEQ ID NOS: 1 and 2)

```
5461 GTATCATCTGTTATATATTCAGGGAACGAAAATATATTTAATGAAAAATATAATGATATA 5520
1821  V   S   S   V   I   Y   S   G   N   E   N   I   F   N   E   K   Y   N   D   I   1840

5521 GGTTTTAAAATAATCGATAATAGGAATGAAAAAGAGAAAGAGAAAAAGAAATGTTTTATT 5580
1841  G   F   K   I   I   D   N   R   N   E   K   E   K   R   K   K   K   G   F   I   1860

5581 GTATTAGGTTGTGGTTGTTATCGTATTGGTAGTTCTGTAGAATTTGATTGGAGTGCTATA 5640
1861  V   L   G   C   G   C   Y   R   I   G   S   S   V   E   F   D   W   S   A   I   1880

5641 CATTGTGTAAAGACCATAAGAAAATTAAACCATAAAGCTATATTAATAAATTGTAACCCA 5700
1881  H   C   V   K   T   I   R   K   L   N   H   K   A   I   L   I   N   C   N   P   1900

5701 GAAACTGTAAGTACAGATTATGATGAAAGTGATCGTCTATATTTTGATGAAATAACAACA 5760
1901  E   T   V   S   T   D   Y   D   E   S   D   R   L   Y   F   D   E   I   T   T   1920

5761 GAAGTTATAAAATTTATATATAACTTTGAAAATAGTAATGGTGTGATTATAGCTTTTGGT 5820
1921  E   V   I   K   F   I   Y   N   F   E   N   S   N   G   V   I   I   A   F   G   1940

5821 GGACAAACATCAAATAATTTAGTATTTAGTTTATATAAAAATAATGTAAATATATTAGGA 5880
1941  G   Q   T   S   N   N   L   V   F   S   L   Y   K   N   N   V   N   I   L   G   1960

5881 TCAGTGCACAAAGTGTTGATTGTTGTGAAAATAGGAATAAATTTTCGCACTTATGTGATT 5940
1961  S   V   H   K   V   L   I   V   V   K   I   G   I   N   F   R   T   Y   V   I   1980

5941 CTTAAAATTGATCAACCGAAATGGAATAAATTTACAAAATTATCCAAGGCTATACAATTT 6000
1981  L   K   I   D   Q   P   K   W   N   K   F   T   K   L   S   K   A   I   Q   F   2000

6001 GCTAATGAGGTAAAATTTCCTGTATTAGTAAGACCATGGTATGTATTATCTGGTGCAGCT 6060
2001  A   N   E   V   X   F   P   V   L   V   R   P   S   Y   V   L   S   G   A   A   2020

6061 ATGAGAGTTGTAAATTGTTTTGAAGAATTAAAAAACTTTTTAATGAAGGCAGCTATTGTT 6120
2021  M   R   V   V   N   C   F   E   E   L   K   N   F   L   M   K   A   A   I   V   2040

6121 AGTAAAGATAATCCTGTTGTAATATCAAAATTTATTGAGAATGCTAAAGAAATAGAAATA 6180
2041  S   K   D   N   P   V   V   I   S   K   F   I   E   N   A   K   E   I   E   I   2060

6181 GATTGTGTTAGTAAAAATGGTAAAATAATTAATTATGCTATATCTGAACATGTTGAAAAT 6240
2061  D   C   V   S   K   N   G   K   I   I   N   Y   A   I   S   E   H   V   E   N   2080

6241 GCTGGTGTACATTCAGGTGATGCAACATTAATATTACCTGCACAAAATATATATGTTGAA 6300
2081  A   G   V   H   S   G   D   A   T   L   I   L   P   A   Q   N   I   Y   V   E   2100

6301 ACACATAGGAAAATAAAGAAAATATCCGAAAAGATTTCAAAATCATTAAATATATCTGGT 6360
2101  T   H   R   K   I   K   K   I   S   E   K   I   S   K   S   L   N   I   S   C   2120

6361 CCATTTAATATACAATTTATATGTCATCAAAATGAAATAAAAATTATTGAATGTAATTTA 6420
2121  P   F   N   I   Q   F   I   C   H   Q   N   E   I   K   I   I   E   C   N   L   2140

6421 AGAGCATCTAGAACTTTTCCATTTATATCAAAAGCTCTAAATCTAAACTTTATAGATTTA 6480
2141  R   A   S   R   T   F   P   F   I   S   K   A   L   N   L   N   F   I   D   L   2160

6481 GCTACAAGGATATTAATGGGTTATGACGTCAAACCAATTAATATATCATTAATTGATTTA 6540
2161  A   T   R   I   L   M   G   Y   D   V   K   P   I   N   I   S   L   I   D   L   2180

6541 GAATATACAGCTGTAAAAGCACCGATTTTCTCATTTAATAGATTACATGGATCAGATTGT 6600
2181  E   Y   T   A   V   K   A   P   I   F   S   F   N   R   L   H   G   S   D   C   2200
```

TABLE 1-continued

Nucleotide and Deduced Amino Acid Sequence of the
Carbamoyl Phosphate Synthetase II Gene from *Plasmodium falciparum* (SEQ ID NOS: 1 and 2)

```
6601 ATACTAGGTGTAGAAATGAAATCTACAGGTGAAGTAGCATGTTTTGGTTTAAATAAATAT 6660
2201  I  L  G  V  E  M  K  S  T  G  E  V  A  C  F  G  L  N  K  Y     2220

6661 GAAGCTTTATTAAAATCATTAATAGCTACAGGTATGAAGTTACCCAAAAAATCAATACTT 6720
2221  E  A  L  L  K  S  L  I  A  T  G  M  K  L  P  K  K  S  I  L     2240

6721 ATAAGTATTAAAAATTTAAATAATAAATTAGCTTTTGAAGAACCGTTCCAATTATTATTT 6780
2241  I  S  I  K  N  L  N  N  K  L  A  F  E  E  P  F  Q  L  L  F     2260

6781 TTAATGGGATTTACAATATATGCGACTGAAGGTACGTATGATTTCTACTCTAAATTTTTA 6840
2261  L  M  G  F  T  I  Y  A  T  E  G  T  Y  D  F  Y  S  K  F  L     2280

6841 GAATCTTTTAATGTTAATAAAGGTTCTAAATTTGATCAAAGACTTATTAAAGTTCATAAT 6900
2281  E  S  F  N  V  N  K  G  S  K  F  H  Q  R  L  I  K  V  H  N     2300

6901 AAAAATGCAGAAAATATATCACCAAATACAACAGATTTAATTATGAATCATAAAGTTGAA 6960
2301  K  N  A  E  N  I  S  F  N  T  T  D  L  I  M  N  H  K  V  E     2320

6961 ATGGTTATTAATATAACTGATACATTAAAAACAAAGGTTAGTTCAAATGGTTATAAAATT 7020
2321  M  V  I  N  I  T  D  T  L  K  T  K  V  S  S  N  G  Y  K  I     2340

7021 AGAAGATTAGCATCAGATTTCCAGGTTCCTTTAATAAGTAATATGAAACTTTGTTCTCTT 7080
2341  K  R  L  A  S  D  F  Q  V  P  L  I  T  N  M  K  L  C  S  L     2360

7081 TTTATTGACTCATTATATAGAAAATTCTCAAGACAAAAGGAAAGAAAATCATTCTATACC 7140
2361  F  I  D  S  L  Y  R  K  F  S  R  Q  K  E  R  K  S  F  Y  T     2380

7141 ATAAAGAGTTATGACGAATATATAAGTTTGGTATAA                           7176
2381  I  K  S  Y  D  E  Y  I  S  L  V  *                            2392

7277 GCAAGAAATTATTCAATAAATTCGATTTAACATTACTTATTTATGTATTTATTAACTTTC 7236

7237 ATTCCATAACAACATGAAAAGTATAAATATATAAATAGTAATATATAATATATAATATAT 7296

7297 ATATATATATATATATATATATTTATTTATTTAATTATATTTACGTTTAAATATTAATAA 7356

7357 ATGTTTTTATTAAATATGATCATTAATTTATATTGATTTATTTTTTTATAAATTTTTGTT 7416

7417 ATATATACAAATTTTATTTATTCACTCATATGTATAAACCAAAATGGTTTTTTCAATTTA 7476

7477 CAAATAATTTTATAATTTTAATAAATTTATTAATTATAAAAAAAATAAAAATATATAAAC 7536

7537 ATTAAAATGTATAAATTCTTTTAATTATATAATAATTTATAAATGTTATGATTTTTTTAA 7596

7597 AAAATTCAACGAAAAAAAAGAGGAACTGTATATACAAAAGGGACTATATATATGTATATA 7656

7657 TATATATATATATATATGTTTTTTTTTCCTTATTCTAGA    7695
```

The GAT domain is make up of two subdomains: a putative structural domain (1-750) and a glutaminase domain (1447–2070). These two subdomains are separated by a first inserted sequence (751–1446, underlined). The two ATP binding subdomains of the synthetase subunit, CPSa (2071–3762) and CPSb (5572–5173) are separated by a second inserted sequence (3763–5571, underlined).

As these inserted sequences are not found in other carbamoyl phosphate synthetase genes they represent prime targets for therapies including, but not limited to, antisense nucleotides, ribozymes and triplex forming nucleotides as there is a decreased likelihood of deleterious reaction with host homologues of the gene.

Antisense RNA molecules are known to be useful for regulating gene expression within the cell. Antisense RNA molecules which are complementary to portion(s) of CPSII can be produced from the CPSII sequence. These antisense molecules can be used as either diagnostic probes to determine whether or not the CPSII gene is present in a cell or can be used as a therapeutic to regulate expression of the CPSII gene. Antisense nucleotides prepared using the CPSII sequence include nucleotides having complementarity to the CPSII mRNA and capable of interfering with its function in vivo and genes containing CPSII sequence elements that can be just transcribed in living cells to produce antisense nucleotides. The genes may include promoter elements from messenger RNA (polymerase II) from cells, viruses, pathogens or structural RNA genes (polymerase I & III) or synthetic promoter elements. A review of antisense design is provided in "Gene Regulation: Biology of Antisense RNA and DNA" R. P. Eirckson and J. G. Izant, Raven Press 1992. Reference may also be had to U.S. Pat. No. 5,208,149 which includes further examples on the design of antisense nucleotides. The disclosure of each of these references is incorporated herein by reference.

As used herein the term "nucleotides" include but are not limited to oligomers of all naturally-occurring deozyribonucleotides and ribonucleotides as well as any nucleotide analogues. Nucleotide analogues encompass all compounds capable of forming sequence-specific complexes (eg duplexes or hetroduplexes) with another nucleotide including methylphosphonates or phosphorothioates but may have advantageous diffusion or stability properties. The definition of nucleotides includes natural or analogue bases linked by phosphodiester bonds, peptide bonds or any other covalent linkage. These nucleotides may be synthesised by any combination of in vivo in living cells, enzymatically in vitro or chemically.

Ribozymes useful in regulating expression of the CPSII gene include nucleotides having CPSII sequence for specificity and catalytic domains to promote the cleavage of CPSII mRNA in vitro or in vivo. The catalytic domains include hammerheads, hairpins, delta-virus elements, ribosome RNA introns and their derivatives. Further information regarding the design of ribozymes can be found in Haseloff, J. & Gerlach, W. L. (1988) Nature 334, 585; Kruger, K., Grabowski, P. J., Zaug, A. J., Sands, J., Gottschling, D. E. & Cech, T. R. (1982) Cell 31, 147; International Patent Application No. WO 88/04300, U.S. Pat. Nos. 4,987,071 and 5,254,678. The disclosure of each of these references is incorporated herein by reference. The catalytic elements may enhance the artificial regulation of a CPSII target mRNA by accelerating degradation or some other mechanism.

Triple helix oligonucleotides can be used to inhibit transcription from the genome. Given the sequence provided herein for the CPSII gene it will now be possible to design oligonucleotides which will form triplexes thereby inhibiting transcription of the CPSII gene. Information regarding the generation of oligonucleotides suitable for triplex formation can be found in a Griffin et al (Science 245: 967–971 (1989)) this disclosure of this reference is incorporated herein by reference.

Triplex agents include all nucleotides capable of binding to the CPSII gene through formation of the complex with DNA or chromatin. The interaction can be through formation of a triple-stranded Hoogsteen structure or other mechanisms such as strand invasion that relies on the CPSII sequence information.

Accordingly, in a fourth aspect the present invention consists in a ribozyme capable of cleaving carbamoyl phosphate synthetase II mRNA, the ribozyme including sequences complementary to portions of mRNA obtained from the nucleic acid molecule of the first aspect of the present invention.

In a preferred embodiment of this aspect of the present invention the ribozyme includes sequences complementary to mRNA obtained from the first or second inserted sequences of the nucleic acid molecule of the first aspect of the present invention.

In a fifth aspect the present invention consists in an antisense oligonucleotide capable of blocking expression of the nucleic acid molecule of the first aspect of the present invention.

As stated above, in one aspect the present invention relates to a method of producing CPSII by rcombinant technology. The protein produced by this method and the polypeptides of the present invention will be useful in in vitro drug binding studies in efforts to develop other anti-malarial therapeutics.

In order that the nature of the present invention may be more clearly understood the method by which the *P. falciparum* CPSII gene was cloned will now be described with reference to the following example and Figures.

BRIEF DESCRIPTION OF THE DRAWINGS

FIG. 1 is a summary of a "gene walking" strategy used to clone and sequence the full length *P. falciparum* carbamoyl phosphate synthetase II gene.

EXAMPLE

The conventional way to screen for genes of which the amino acid sequence had not been previously determined is via heterologous probing, i.e. with gene fragments of the target enzyme from closely related organisms. This has proved to be unsuccessful for several workers with *Plasmodium falciparum* largely due to the unusually high A–T content of its genome. After initial unfruitful attempts to isolate the CPSII gene in *Plasmodium falciparum* using a yeast ura2 gene fragment (Souciet et al., 1989), the present invention opted to amplify part of the CPSII gene using the polymerase chain reaction (PCR) (Saiki et al.,1988) with a view to use the amplified product as probe for screening.

The present invention isolated and cloned a PCR product using oligonucleotides designed from conserved sequences from the amino terminal GAT domain and the first half of the synthetase domain of the CPS gene. Nucleotide sequencing confirmed that a portion of the CPSII gene had been obtained. Total parasite DNA was fragmented with a restriction enzyme and subjected to Southern analysis using the CPSII-specific gene probe. The sizes of DNA fragments hybridizing to the gene probe were determined then the DNA in the corresponding bands were used for the construction of a "mini-library". In this way a smaller population of clones were screened for the pf CPSII gene.

To isolate the full length of pf CPSII gene, a series of mini-libraries were constructed utilising different segments of known sequence to gain information of the unknown flanking regions both towards the 5' and 3' termini of the gene using "gene-walking". The strategy employed is summarized in FIG. 1.

In the first Southern analysis, total *P. falciparum* DNA was digested with HindIII and EcoRI and hybridisation was carried out using the pfCPSII 453 PCR product. A 3.0 kb HindIII and a smaller EcoRI fragment hybridised to the probe. Subsequent screening of a HindIII pTZ18U mini-library resulted in the isolation of a recombinant that contained a 3.0 kb pfCPSII gene fragment, CPS2. The 453 bp PCR product was localised in the middle of this segment.

Two regions from both the 5' and 3' ends of CPS2 were used to isolate neighbouring sequences at either end in order to obtain the further gene sequences. A HindIII/EcoRI fragment from the 5' end of CPS2 was instrumental in isolating a further 1.5 kb fragment, CPS1 consisting of the complete 5' region of the gene and some non-encoding sequences.

A 550 bp inverse PCR (IPCR; Triglia et al., 1988) product was obtained with the aid of known sequences from the 3' end of CPS2.

This IPCR product was used to screen for the 3' region flanking CPS2. A 3.3 kb HindIII recombinant containing CPS3 as well as a related 3.3 kb XBaI clone (not presented in FIG. 1) were isolated by the mini-library technique. Using a 200 bp XbaI/HindIII fragment from the 3' end of CPS3, a 1.3 kb XbaI segment, CPS4 was cloned which contained the putative stop codon and some 3' non-coding region.

Combining these four gene gragments (CPS1, CPS2, CPS3 and CPS4) excluding their overlaps, gives a total of 8.8 kb consisting of approximately 7.0 kb coding and 1.8 flanking sequences.

The complete nucleotide sequence of the CPSII gene in *P. falciparum*, together with its 5' and 3' flanking sequences, is presented in Table 1.

As will be readily appreciated by those skilled in the art the isolation of this gene and its sequencing by the present inventors opens up a range of new avenues for treatment of *Plasmodium falciparum* infection. The present invention enables the product of quantities of the *Plasmodium falciparum* carbamoyl phosphate synthetase II enzyme using recombinant DNA technology. Characterisation of this enzyme may enable its use as a chemotherapeutic loci.

The isolation of this gene also will enable the production of antisense molecules, ribozymes or other gene inactivation agents which can be used to prevent the multiplication of the parasite in infected individuals.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

Cox, F. E. G. (1991) Malaria vaccines: while we are waiting. Parasitology Today 7: 189–190

Gero, A. M. and O'Sullivan, W. J. (1991) Purines and pyrimidines in malarial parasites. Blood Cells 16: 467–498

Hammond, D. J. Burchell, J. R. and Pudrey, M. (1985) Inhibition of pyrimidine biosynthesis de novo in *Plasmodium falciparum* by 2.(4.t-butylcyclohexyl)-3-hydroxy-1, 4-naphthoquinine in vitro. Mol. Biochem. Parasitol 14: 97–109

Hill, B., Kilsby, J. Rogerson, G. W., McIntosh, R. T. and Ginger, C. D. (1981). The Enzymes of pyrimidine biosynthesis in a range of parasitic protozoa and helminths. Mol. Biochem. Parasitol. 2: 123–134.

Johnson, C. Malaria back to plague us. Sydney Morning Herald, Nov. 13, 1991.

Jones, M. E. (1980) Pyrimidine nucleotide biosynthesis in animals: genes, enzymes and regulation of UMP biosynthesis. Annu. Rev. Biochem. 49: 253–279.

Krungkrai, J. Cerami, A. and Henderson, G. B. (1990) Pyrimidine biosynthesis in parasitic protozoa: purification of a monofunctional dihydroorotase from *Plasmodium berghei* and *Crithidia fasciculata*. Biochemistry 29: 6270–6275.

Krungkrai, J. Krungkrai, S. R. and Phakanont, K. (1992) Antimalarial activity of orotate analogs that inhibit dihydrootase and dihydroorotate dehydrogenase. Biochem. Pharmacol. 43: 1295–1301.

Marshal, E. (1991) Malaria parasite gaining ground against science. Science 2: 190.

Nyunoya, H., Broglie, K. E., Widgren, W. E. and Lusty C. J. (1985) Characterization and derivation of the gene coding for mitochondrial carbamyl phosphate synthetase I of rat. J. Biol. Chem. 260: 9346–9356.

Prapunwattana, P., O'Sullivan, W. J. and Yuthavong, Y. (1988) Depression of *Plasmodium falciparum* dihydroorotate dehydrogenase activity in in vitro culture by tetracycline. Mol. Biochem. 27: 119–124.

Queen, S. A., Vander Jagt, D. L. and Reyes, P. (1990) In vitro susceptibilities of *Plasmodium falciparum* to compounds which inhibit nucleotide metabolism. Antimicrob. Agents Chemother. 34: 1393–1398.

Reyes, P., Rathod, P. K., Sanchez, D. J. Mrema, J. E. K., Rieckmann, K. H. and Heidrich, H. G. (1982) Enzymes of purine and pyrimidine metabolism from the human malaria parasite, *Plasmodium falciparum*. Mol. Biochem. Parasitol. 5: 275–290.

Rubino S. D., Nyunoya, H. and Lusty, C. J. (1986) JBC 261(24):11320–11327.

Saiki, R. K., Gelfand, D. H., Stoffel, S., Scharf, S. J., Higuchi, R., Horn, G. T., Mullis K. B. and Erlich H. A. (1988) Science 239:487–491.

Scott, H. V., Gero, A. M. and O'Sullivan, W. J. (1986) In vitro inhibition of *Plasmodium falciparum* by pyrazofurin, an inhibitor of pyrimidine biosynthesis de novo. Mol. Biochem. Parasitol. 18: 3–15.

Sherman, I. W. (1979) Biochemistry of Plasmodium (malarial parasites) Microbiol. Rev. 43: 453–495.

Simmer, J. P., Kelly, R. E., Rinker, Jr., A. G., Scully, J. L. and Evans D. R. (1990) Mammalian carbamyl phosphate synthetase (CPS). J. Biol. Chem 265: 10395–10402.

Simmer, J. P., Kelly, R. E., Austin, G. R., Jr., Scully, J. L. and Evans, D. R. (1990) JBC 285(18):10395–10402.

Souciet, J. L., Nagy, M., Le Gouar, M., Lacroute, F. and Potier, S. (1989) Gene (Amst.) 79: 59–70.

Triglia, T., Peterson, M. G. and Kemp, D. J. (1988) PNAS 16:8186.

Werner, M., Feller, A. and Pierard, A. (1985) Nucleotide sequence of yeast gene CPA1 encoding the small subunit of argine-pathway carbamoyl-phosphate synthetase. Eur. J. Biochem. 146: 371–381.

We claim:

1. An isolated nucleic acid molecule encoding *Plasmodium falciparum* carbamoyl phosphate synthetase II, or a portion thereof, wherein the sequence of the nucleic acid molecule comprises a sequence selected from the group consisting of nucleotides 1226 to 8401, nucleotides 1226 to 1975, nucleotides 1976 to 2671, nucleotides 2672 to 3295, nucleotides 3296 to 4987, nucleotides 4988 to 6796, nucleotides 6797 to 8398, nucleotides 1226 to 4585, nucleotides 3296 to 7891, and nucleotides 3296 to 8398 of SEQ. ID. NO: 1.

2. The nucleic acid molecule of claim 1 wherein the sequence of the nucleic acid molecule comprises SEQ. ID. NO: 1.

3. A vector comprising the nucleic acid of claim 1.

4. A vector comprising the nucleic acid of claim 3.

* * * * *